US010799616B2

(12) United States Patent
Shoseyov et al.

(10) Patent No.: US 10,799,616 B2
(45) Date of Patent: Oct. 13, 2020

(54) CROSS-LINKED RESILIN-CONTAINING MATERIALS

(71) Applicants: CollPlant Ltd., Nes Ziona (IL); Yissum Research Development Company of the Hebrew University of Jerusalem Ltd., Jerusalem (IL)

(72) Inventors: Oded Shoseyov, Karme Yosef (IL); Sigal Meirovitch, Tel-Aviv (IL); Shaul Lapidot, Kibbutz Tzora (IL); Amit Rivkin, Beer-Yaacov (IL)

(73) Assignees: CollPlant Ltd., Rehovot (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 989 days.

(21) Appl. No.: 15/034,646

(22) PCT Filed: Nov. 5, 2014

(86) PCT No.: PCT/IL2014/050963
§ 371 (c)(1),
(2) Date: May 5, 2016

(87) PCT Pub. No.: WO2015/068160
PCT Pub. Date: May 14, 2015

(65) Prior Publication Data
US 2016/0279295 A1   Sep. 29, 2016

Related U.S. Application Data

(60) Provisional application No. 61/899,951, filed on Nov. 5, 2013.

(51) Int. Cl.
| A61K 36/00 | (2006.01) |
| A61L 26/00 | (2006.01) |
| A61L 27/48 | (2006.01) |
| A61L 27/56 | (2006.01) |
| C08J 3/00  | (2006.01) |
| C08L 89/00 | (2006.01) |
| A61L 27/26 | (2006.01) |
| C07K 14/435 | (2006.01) |
| C07K 14/78 | (2006.01) |

(52) U.S. Cl.
CPC ............ *A61L 27/48* (2013.01); *A61L 27/26* (2013.01); *A61L 27/56* (2013.01); *C07K 14/43563* (2013.01); *C07K 14/78* (2013.01); *C08J 3/00* (2013.01); *C08L 89/00* (2013.01); *A61L 2430/00* (2013.01)

(58) Field of Classification Search
CPC ......... C07K 14/78; A61K 35/64; A61K 36/00
See application file for complete search history.

(56) References Cited

U.S. PATENT DOCUMENTS

| 2002/0153632 A1* | 10/2002 | Schaufler .............. A61L 15/225 264/50 |
| 2010/0317588 A1 | 12/2010 | Shoseyov et al. |
| 2015/0013299 A1* | 1/2015 | Haj-Ali ................. D06M 13/00 57/244 |

FOREIGN PATENT DOCUMENTS

| IL | 206004 | 8/2015 |
| IL | 219461 | 6/2016 |
| WO | WO 2004/104043 | 12/2004 |
| WO | WO 2009/069123 | 6/2009 |
| WO | WO 2013/030840 | 3/2013 |
| WO | WO 2015/068160 | 5/2015 |

OTHER PUBLICATIONS

Office Action dated Apr. 18, 2018 From the Israel Patent Office Re. Application No. 245503 and Its Translation Into English. (4 Pages).
Supplementary European Search Report and the European Search Opinion dated Mar. 29, 2017 From the European Patent Office Re. Application No. 14860295.6. (8 Pages).
Notification of Office Action and Search Report dated Feb. 24, 2018 From the State Intellectual Property Office of the People's Republic of China Re. Application No. 201480072164.3 and Its Translation of Office Action Into English. (13 Pages).
Office Action dated Aug. 22, 2018 From the Israel Patent Office Re. Application No. 245503 and Its Translation Into English. (5 Pages).
International Preliminary Report on Patentability dated May 19, 2016 From the International Bureau of WIPO Re. Application No. PCT/IL2014/050963.
International Search Report and the Written Opinion dated Feb. 9, 2015 From the International Searching Authority Re. Application No. PCT/IL2014/050963.
Bagnaninchi et al. "Tissue Engineering for Tendon Repair", British Journal of Sports Medicine, 41: e10-1-e10-5, Published Online Oct. 24, 2006.
Benedetti et al. "Production of Micronic Particles of Biocompatible Polymer Using Supercritical Carbon Dioxide", Biotechnology and Bioengineering, 53: 232-237, 1997.

(Continued)

*Primary Examiner* — Maryam Monshipouri

(57) ABSTRACT

Disclosed herein is a compositions-of-matter comprising a cross-linked polymer, the cross-linked polymer comprising a plurality of resilin polypeptide moieties, and at least one polymeric moiety covalently cross-linked to a plurality of the resilin polypeptide moieties via at least one cross-linking moiety, the cross-linking moiety being devoid of a biphenyl moiety. Further disclosed herein is a process for preparing the composition-of-matter, a composite material comprising the composition-of-matter and at least one additional polymeric substance bound to the cross-linked polymer, an article-of-manufacturing comprising the composition-of-matter and/or composite material, and a method of treating tissue damage or loss by implanting said article-of-manufacturing in a subject.

15 Claims, 8 Drawing Sheets

Specification includes a Sequence Listing.

(56) References Cited

OTHER PUBLICATIONS

Bennet-Clark et al. "The Jump of the Flea: A Study of the Energetics and a Model of the Mechanism", Journal of Experimental Biology, 47: 59-76, 1967.
Burrows et al. "Resilin and Chitinous Cuticle Form a Composite Structure for Energy Storage in Jumping by Froghopper Insects", BMC Biology, 6(41): 1-16, Sep. 30, 2008.
Butler et al. "Functional Tissue Engineering for Tendon Repair: A Multidisciplinary Strategy Using Mesnechymal Stem Cells, Bioscaffolds, and Mechanical Stimulation", Journal of Orthopaedic Research, 26: 1-9, Jan. 2008.
Charati et al. "Hydrophilic Elastomeric Biomaterials Based on Resilin-Like Polypeptides", Soft Matter, 5(18): 3412-3416, 2009.
Elvin et al. "Synthesis and Properties of Crosslinked Recombinant Pro-Resilin", Nature, 437: 999-1002, Oct. 13, 2005.
Fancy et al. "Chemistry for the Analysis of Protein-Protein Interactions: Rapid and Efficient Cross-Linking Triggered by Long Wavelength Light", Proc. Natl. Acad. Sci. USA, 96: 6020-6024, May 1999.
Freitas et al. "Microencapsulation by Solvent Extraction/ Evaporation: Reviewing the State of the Art of Microsphere Preparation Process Technology", Journal of Controlled Release, 102: 313-332, 2005.
Gedanken "Preparation and Properties of Proteinaceous Microspheres Made Sonochemically", Chemistry A European Journal, 14: 3840-3853, 2008.
Gosline et al. "Elastic Proteins: Biological Roles and Mechanical Properties", Philosophical Transactions of the Royal Society B: Biological Sciences, 357(1418): 121-132, Feb. 28, 2002.
Haas et al. "The Function of Resilin in Beetle Wings", Proceedings of the Royal Society B: Biological Sciences, 267(1451): 1375-1381, Jul. 22, 2000.
McGann et al. "Resilin-Based Hybrid Hydrogels for Cardiovascular Tissue Engineering", Macromolecules, 214(2): 203-213, Jan. 25, 2013.
Moutos et al. "Composite Scaffolds for Cartilage Tissue Engineering", Biorheology, 45(3-4): 501-512, 2008.
Qin et al. "Expression, Cross-Linking, and Characterization of Recombinant Chitin Binding Resilin", Biomacromolecules, 10: 3227-3234, 2009.
Qin et al. "Recombinant Exon-Encoded Resilins for Elastomeric Biomaterials", Biomaterials, 32: 9231-9243, 2011.
Ruckenstein et al. "Sedimentation Polymerization", Polymer, 36(14): 2857-2860, 1995.
Shah et al. "Designer Emulsions Using Microfluidics", MaterialsToday, 11(4): Apr. 18-27, 2008.
Velema et al. "Biopolymer-Based Biomaterials as Scaffolds for Tissue Engineering", Advances in Biochemical Engineering/ Biotechnology, 102: 187-238, 2006.
Vincent et al. "Design and Mechanical Properties of Insect Cuticle", Arthropod Structure & Development, 33: 187-199, 2004.
Ward et al. "Amine Functionalization of Collagen Matrices With Multifunctional Polyethylene Glycol Systems", Biomacromolecules, 11: 3093-3101, 2010. Abstract.
Weis-Fogh "A Rubber-Like Protein in Insect Cuticle", The Journal of Experimental Biology, p. 889-907, 1960.
Weis-Fogh "Molecular Interpretation of the Elasticity of Resilin, A Rubber-Like Protein", Journal of Molecular Biology, 3: 648-667, 1961.
Weis-Fogh "Thermodynamic Properties of Resilin, A Rubber-Like Protein", Journal of Molecular Biology, 3: 520-531, 1961.
Young et al. "The Role of the Tymbal in Cicada Sound Production", The Journal of Experimental Biology, 198: 1001-1019, 1995.
Notification of Office Action dated Nov. 15, 2018 From the State Intellectual Property Office of the People's Republic of China Re. Application No. 201480072164.3 and Its Translation Into English. (7 Pages).
Notification of Office Action dated Jun. 5, 2019 From the State Intellectual Property Office of the People's Republic of China Re. Application No. 201480072164.3. (4 Pages).
Translation of Notification dated Jun. 20, 2019 From OA dated Jun. 5, 2019 From the State Intellectual Property Office of the People's Republic of China Re. Application No. 201480072164.3. (2 Pages).
Notification of Office Action and Search Report dated Feb. 3, 2020 From the State Intellectual Property Office of the People's Republic of China Re. Application No. 201480072164.3. (6 Pages).
Translation of Notification dated Mar. 11, 2020 From OA dated Feb. 3, 2020 From the State Intellectual Property Office of the People's Republic of China Re. Application No. 201480072164.3. (2 Pages).
Li et al. "Preparation of Nano-Crystalline Cellulose by Chemical Methods", Journal of Nanjing Forestry University—Natural Science Edition, 36(5): 161-166, Sep. 2012. English Abstract.

* cited by examiner

```
catatgtcgtactaccatcaccatcaccatcacgattacgatatcccaacgaccgaaaac
     M  S  Y  Y  H  H  H  H  H  H  D  Y  D  I  P  T  T  E  N
ctgtattttcagggcgccatgggacaggagccaccagttaactcgtatctacctccgtcc
  L  Y  F  Q  A  M  G  P  E  P  P  V  N  S  Y  L  P  P  S
gatagctatggagcaccgggtcagagtggtcccggcggcaggccgtcggattcctatgga
  D  S  Y  G  A  P  G  Q  S  G  P  G  G  R  P  S  D  S  Y  G
gctcctggtggtggaaacggtggacggccctcagacagctatggcgctccaggccagggt
  A  P  G  G  G  N  G  G  R  P  S  D  S  Y  G  A  P  G  Q  G
caaggacagggacaaggacaaggtggatatgcaggcaagccctcagataccatatggagct
  Q  G  Q  G  Q  G  Q  G  G  Y  A  G  K  P  S  D  T  Y  G  A
cctggtggtggaaatggcaacggaggtcgtccatcgagcagctatggcgctcctggcggt
  P  G  G  G  N  G  N  G  G  R  P  S  S  S  Y  G  A  P  G  G
ggaaacggtggtcgtccttcggatacctacggtgctcctggtggcggaaatggtggacgc
  G  N  G  G  R  P  S  D  T  Y  G  A  P  G  G  N  G  G  R
ccatcggacacttatggtgctcctggtggtggtggaaatggcaacggcggacgaccttca
  P  S  D  T  Y  G  A  P  G  G  G  N  G  N  G  G  R  P  S
agcagctatggagctcctggtcaaggacaaggcaacggaaatggcggtcgctcatcgagc
  S  S  Y  G  A  P  G  Q  G  Q  G  N  G  N  G  G  R  S  S
agctatggtgctcctggcggtggaaacggcggtcgtccttcggatacctacggtgctccc
  S  Y  G  A  P  G  G  G  N  G  G  R  P  S  D  T  Y  G  A  P
ggtggtggaaacggtggtcgtccttcggatacttacggcgctcctggtggcggcaataat
  G  G  G  N  G  G  R  P  S  D  T  Y  G  A  P  G  G  N  N
ggcggtcgtcctcaagcagctacggcgctcctggtggtggaaacggtggtcgtccatct
  G  G  R  P  S  S  S  Y  G  A  P  G  G  G  N  G  G  R  P  S
gacacctatggcgctcctggtggcggtaacggaaacggcagcggtggtcgtccttcaagc
  D  T  Y  G  A  P  G  G  G  N  G  N  G  S  G  R  P  S  S
agctatggagctcctggtcagggccaaggtggatttggtggtcgtccatcggactcctat
  S  Y  G  A  P  G  Q  G  Q  G  G  F  G  G  R  P  S  D  S  Y
ggtgctcctggtcagaaccaaaaaccatcagattcatatggcgcccctggtagcggcaat
  G  A  P  G  Q  N  Q  K  P  S  D  S  Y  G  A  P  G  S  G  N
ggcaacggcggacgtccttcgagcagctatggagctccaggctcaggacctggtggccga
  G  N  G  G  R  P  S  S  S  Y  G  A  P  G  S  G  P  G  G  R
ccctccgactcctacggaccccccagcttctggatcggagcaggtggcgctggaggcagt
  P  S  D  S  Y  G  P  P  A  S  G  S  G  A  G  G  A  G  G  S
ggaccccggcggcgctgactacgataacgatgagggggatccccgaccccggcatggcagcg
  G  P  G  G  A  D  Y  D  N  D  E  G  I  P  D  P  G  M  A  A
acatcatcaatgtcagttgaattttacaactctaacaaatcagcacaaacaaactcaatt
  T  S  S  M  S  V  E  F  Y  N  S  N  K  S  A  Q  T  N  S  I
acaccaataatcaaaattactaacacatctgacagtgatttaaatttaaatgacgtaaaa
  T  P  I  I  K  I  T  N  T  S  D  S  D  L  N  L  N  D  V  K
gttagatattattacacaagtgatggtacacaaggacaaactttctggtgtgaccatgct
  V  R  Y  Y  Y  T  S  D  G  T  Q  G  Q  T  F  W  C  D  H  A
ggtgcattattaggaaatagctatgttgataacactagcaaagtgacagcaaacttcgtt
  G  A  L  L  G  N  S  Y  V  D  N  T  S  K  V  T  A  N  F  V
aaagaaacagcaagcccaacaatcaacctatgatacatatgttgaatttggatttgcaagc
  K  E  T  A  S  P  T  S  T  Y  D  T  Y  V  E  F  G  F  A  S
ggacgagctactcttaaaaaaggacaatttataacgattcaaggaagaataacaaaatca
  G  R  A  T  L  K  K  G  Q  F  I  T  I  Q  G  R  I  T  K  S
gactggtcaaactacactcaaacaaatgactattcatttgatgcaagtagttcaacacca
  D  W  S  N  Y  T  Q  T  N  D  Y  S  F  D  A  S  S  S  T  P
gttgtaaatccaaaagttacaggatatataggtggaggctaaagtacttggtacagcacca
  V  V  N  P  K  V  T  G  Y  I  G  G  A  K  V  L  G  T  A  P
taggatcgatccagatgtac
*
```

FIG. 1

CROSS-LINKED RESILIN-CONTAINING MATERIALS

RELATED APPLICATIONS

This application is a National Phase of PCT Patent Application No. PCT/IL2014/050963 having International filing date of Nov. 5, 2014, which claims the benefit of priority under 35 USC § 119(e) of U.S. Provisional Patent Application No. 61/899,951 filed on Nov. 5, 2013. The contents of the above applications are all incorporated by reference as if fully set forth herein in their entirety.

SEQUENCE LISTING STATEMENT

The ASCII file, entitled 66107SequenceListing.txt, created on May 5, 2016, comprising 44,880 bytes, submitted concurrently with the filing of this application is incorporated herein by reference.

FIELD AND BACKGROUND OF THE INVENTION

The present invention, in some embodiments thereof, relates to the field of polymeric materials, and, more particularly, but not exclusively, to materials comprising elastic biopolymers and uses thereof.

Fibrous proteins are of great interest in reconstructive medicine research. Natural connective tissue proteins, such as collagen and elastin, have already been tested and utilized in a variety of tissue engineering applications.

As collagen is the major component of the extracellular matrix (ECM), it is the most widely used fibrous protein for tissue engineering. It has been employed in absorbable sutures, sponge wound and burn dressings, drug delivery microspheres, and soft-tissue augmentation in a variety of forms: films, strips, sheets, sponges, beads, discs and more [Velema & Kaplan, Adv Biochem Eng Biotechnol 2006, 102:187-238].

Attempts at regenerating connective tissues have been performed using single component scaffolds, mainly type I collagen scaffolds from animal sources. However, these scaffolds have had limited success as they failed to provide sufficient mechanical support, and subsequently were not able to induce correct tissue architecture [Moutos & Guilak, Biorheology 2008, 45:501-512; Stevens, Materials Today 2008, 11:18-25; Bagnaninchi et al., British Medical Journal 2007, 41:e10; Butler et al., J Orthop Res 2008, 26:1-9].

Elastin is produced in vertebrates in association with collagen in connective tissues such as skin and cartilage. It is also a major component in arteries, allowing the blood vessels to smooth the pulsatile flow of blood from the heart into a continual and steady flow [Gosline et al., Philos Trans R Soc Lond B Biol Sci 2002, 357:121-132]. Although elastin is nearly as common in mammalians as is collagen, the application in reconstructive medicine of elastin from animal sources is far less developed than that of collagen due to preliminary purification difficulties caused by elastin's tendency to calcify, and to contamination with associated microfibrillar proteins which can lead to an immunological response [Velema & Kaplan, Adv Biochem Eng Biotechnol 2006, 102:187-238].

Resilin is found in specialized cuticle regions in many insects, especially in areas where high resilience and low stiffness are required, and serves as an energy storage system. It is best known for its roles in insect flight and in the remarkable jumping ability of fleas and spittlebugs.

Resilin displays unique mechanical properties that combine reversible deformation with very high resilience. It has been reported to be the most elastic biomaterial known [Weis-Fogh, J Mol Biol 1961, 3:520-531; Weis-Fogh, J Mol Biol 1961, 3:648-667].

Efforts have been made towards the use of recombinant resilin as a biopolymer-based scaffold for tissue engineering applications. In nature, resilin forms conformationally free 3-dimensional networks stabilized by di/tri-tyrosine bridges which are formed by enzymatically catalyzed tyrosine oxidation. Methods for analogous in vitro cross-linking of tyrosine residues have been proposed, which have been reported to successfully mimic elastic properties of the native protein upon photochemical cross-linking [Elvin et al., Nature 2005, 437:999-1002; Qin et al., Biomaterials 2011, 32:9231-9243] and peroxidase-catalyzed cross-linking [Qin et al., Biomacromolecules 2009, 10:3227-3234; Qin et al., Biomaterials 2011, 32:9231-9243] of resilin.

Charati et al. [Soft Matter 2009, 5:3412-3416] describe recombinant resilin-like peptides (RLP) where the tyrosines were replaced with phenylalanine and lysine, cross-linked with [tris(hydroxymethyl)phosphino]propionic acid (THPP) and reactive hydroxymethylphosphine (HMP). The cross-linked material was reported to be highly elastic.

International Patent Application No. PCT/IL2008/001542 (published as WO 2009/069123) describes polypeptides comprising an amino acid sequence encoding a monomer of a fibrous polypeptide (such as resilin, elastin, spider silk, silk-worm silk, collagen and mussel byssus protein) attached to a heterologous polysaccharide binding domain, as well as composites comprising a fibrous polypeptide and a polysaccharide.

International Patent Application No. PCT/IL2012/050340 describes polymers comprising a biopolymer (such as a resilin sequence) and a dihydroxyphenyl moiety, and cross-linked polymers comprising cross-linked dihydroxyphenyl moieties. Cross-linking may be effected by oxidation of dihydroxyphenyl moieties. The polymers may be used in the form of an adhesive activated by an oxidizing agent. Similar polymers are also described in Qin et al. [Biomaterials 2011, 32:9231-9243].

Qin et al. [Biomacromolecules 2009, 10:3227-3234; Biomaterials 2011, 32:9231-9243] have reported that non-cross-linked resilin has a similar modulus of elasticity to cross-linked resilin, as determined by nano-indentation, and suggested that the production of highly resilient materials is not entirely dependent upon the di-tyrosine cross-links which occur in native resilin.

Cross-linking between carboxylic groups and primary amines may be obtained using coupling agents such as carbodiimide, uronium and phosphonium reagents. One such carbodiimide coupling reagent for forming a covalent amide bond is 1-ethyl-3-[3-dimethylaminopropyl]carbodiimide (known in the art as EDC or EDAC), which may be used with N-hydroxysuccinimide (NHS) as an activator.

Collagen scaffolds which were cross-linked using EDC/NHS or EDC/NHS/8-arm amine-terminated PEG have been reported to exhibit higher biocompatibility in comparison to glutaraldehyde-cross-linked collagen scaffolds [Ward et al., Biomacromolecules 2010 11:3093-3101].

Additional background art includes: International Patent Application Publication WO 2004/104043; Benedetti et al. [Biotechnol Bioeng 1997, 53:232-237]; Bennet-Clark & Lucey [J Exp Biol 1967, 47:59-76]; Burrows et al. [BMC Biology 2008, 6:41]; Haas et al. [Proc Biol Sci 2000, 267:1375-1381]; Fancy & Kodadek [Proc Natl Acad Sci USA 1999, 96:6020]; Freitas et al. [Journal of Controlled

*Release* 2005, 102:313-332]; Gedanken [*Chem Eur J* 2008, 14:3840-3853]; Ruckenstein et al. [*Polymer* 1995, 36:2857-2860]; Weis-Fogh [*Exp Biol* 1960, 37:889-907]; Vincent & Wegst [*Arthropod Struct Dev* 2004, 33:187-199]; and Young & Bennet-Clark [*J Exp Biol* 1995, 198: 1001-1020].

SUMMARY OF THE INVENTION

According to an aspect of some embodiments of the invention, there is provided a composition-of-matter comprising a cross-linked polymer, the cross-linked polymer comprising a plurality of resilin polypeptide moieties and at least one polymeric moiety covalently cross-linked to at least a portion of the plurality of the resilin polypeptide moieties via at least one cross-linking moiety, the cross-linking moiety being devoid of a biphenyl moiety.

According to an aspect of some embodiments of the invention, there is provided a composite material comprising a composition-of-matter described herein, and at least one additional polymeric substance bound to the cross-linked polymer.

According to an aspect of some embodiments of the invention, there is provided an article-of-manufacturing comprising a composition-of-matter described herein and/or a composite material described herein.

According to an aspect of some embodiments of the invention, there is provided a method of treating tissue damage or loss in a subject in need thereof, the method comprising implanting an article-of-manufacturing described herein in the subject, thereby treating the tissue damage or loss.

According to an aspect of some embodiments of the invention, there is provided a process of preparing a composition-of-matter described herein, the process comprising covalently cross-linking a resilin polypeptide, to at least one polymeric substance, wherein the cross-linking does not produce a biphenyl moiety.

According to some of any one of the embodiments described herein, the resilin polypeptide moieties comprise resilin, a fragment thereof and/or a homologous polypeptide thereof.

According to some embodiments of the invention, at least 10 weight percents of the cross-linked polymer is the at least one polymeric moiety.

According to some embodiments of the invention, the cross-linking moiety comprises an amide bond.

According to some embodiments of the invention, the cross-linking moiety consists of an amide bond.

According to some embodiments of the invention, the at least one polymeric moiety comprises a plurality of amine groups, and the amide bond is formed from at least one amine group of the polymeric moiety and at least one carboxylic group of the resilin polypeptide moiety.

According to some embodiments of the invention, the carboxylic group forms a part of a side chain of an amino acid residue of the resilin polypeptide selected from the group consisting of a glutamate residue and an aspartate residue.

According to some embodiments of the invention, the at least one polymeric moiety comprises a polypeptide.

According to some embodiments of the invention, the polypeptide comprises a collagen (e.g., collagen, a fragment thereof or a homologous polypeptide thereof).

According to some embodiments of the invention, the cross-linking moiety is generated from a side chain of at least one lysine residue of the polymeric moiety.

According to some embodiments of the invention, the at least one polymeric moiety comprises poly(ethylene glycol) (PEG).

According to some embodiments of the invention, the at least one polymeric moiety comprises a branched amine-terminated polymer.

According to some embodiments of the invention, the cross-linked polymer is in a form of a plurality of particles.

According to some embodiments of the invention, a diameter of the particles is in a range of from 1 μm to 200 μm.

According to some embodiments of the invention, the particles are substantially spheroid.

According to some embodiments of the invention, the particles are covalently cross-linked to one another.

According to some embodiments of the invention, the composition-of-matter is in a form of a membrane.

According to some embodiments of the invention, the additional polymeric substance comprises a polysaccharide, and the cross-linked polymer comprises a polysaccharide-binding domain which binds to the polysaccharide.

According to some embodiments of the invention, the resilin polypeptide moieties comprise the polysaccharide-binding domain.

According to some embodiments of the invention, the polysaccharide comprises cellulose.

According to some embodiments of the invention, the composition-of-matter and/or composite material is in a form of a foam.

According to some embodiments of the invention, the composition-of-matter and/or composite material has at least one characteristic selected from the group consisting of:
  an elastic modulus of at least 2.5 kPa; and
  a resilience of at least 50%,
  upon compression of the foam.

According to some embodiments of the invention, the cross-linked polymer is in a form of a plurality of particles, the particles being embedded in the at least one additional polymeric substance.

According to some embodiments of the invention, the additional polymeric substance is covalently linked to the cross-linked polymer.

According to some embodiments of the invention, the additional polymeric substance is covalently linked to the cross-linked polymer via at least one amide bond.

According to some embodiments of the invention, the additional polymeric substance comprises collagen.

According to some embodiments of the invention, the article-of-manufacturing is a medical device.

According to some embodiments of the invention, the medical device is an implantable medical device.

According to some embodiments of the invention, the article-of-manufacturing is capable of forming a scaffold within the subject and thereby inducing a formation of a tissue.

According to some embodiments of the invention, the at least one polymeric substance comprises a plurality of amine groups, and the cross-linking comprises reacting the amine group with a carboxylic group of the resilin polypeptide so as to form an amide bond.

According to some embodiments of the invention, the reacting comprises activating the carboxylic group of the resilin polypeptide, and contacting the resilin polypeptide with the at least one polymeric substance.

According to some embodiments of the invention, the activating is effected by reaction with a carbodiimide.

According to some embodiments of the invention, the process further comprises contacting the resilin polypeptide and the at least one polymeric substance with at least one additional polymeric substance prior to the cross-linking, to thereby produce a composite material which comprises the cross-linked polymer bound to the at least one additional polymeric substance.

According to some embodiments of the invention, the at least one additional polymeric substance is in a form of a foam.

According to some embodiments of the invention, the process further comprises contacting a hydrophilic solution comprising the resilin polypeptide and the at least one polymeric substance with a hydrophilic surface prior to the cross-linking, so as to produce the composition-of-matter in a form of a membrane.

According to some embodiments of the invention, the process further comprises preparing a plurality of particles comprising the resilin polypeptide and the at least one polymeric substance prior to the cross-linking, to thereby produce particles comprising the cross-linked polymer upon the cross-linking.

According to some embodiments of the invention, the particles are covalently cross-linked to one another.

According to some embodiments of the invention, the process further comprises embedding the particles in at least one additional polymeric substance, to thereby produce a composite material which comprises the particles embedded in the at least one additional polymeric substance.

According to some embodiments of the invention, preparing the particles comprises dispersion and/or sedimentation of a mixture of the resilin polypeptide and the at least one polymeric substance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents an exemplary DNA sequence (SEQ ID NO: 12) and protein sequence (SEQ ID NO: 13) of 6H-tagged resilin (exon 1) fused to a cellulose-binding domain (CBD), showing a His tag (underline), a spacer (wavy underline), a TEV protease cleavage sequence (double underline, cleavage site is between the gray QG), amino acids added from the cloning process (dashed underline), native resilin linker (bold underline) and cellulose-binding domain (bold wavy underline);

DESCRIPTION OF SPECIFIC EMBODIMENTS OF THE INVENTION

Figure 2A:
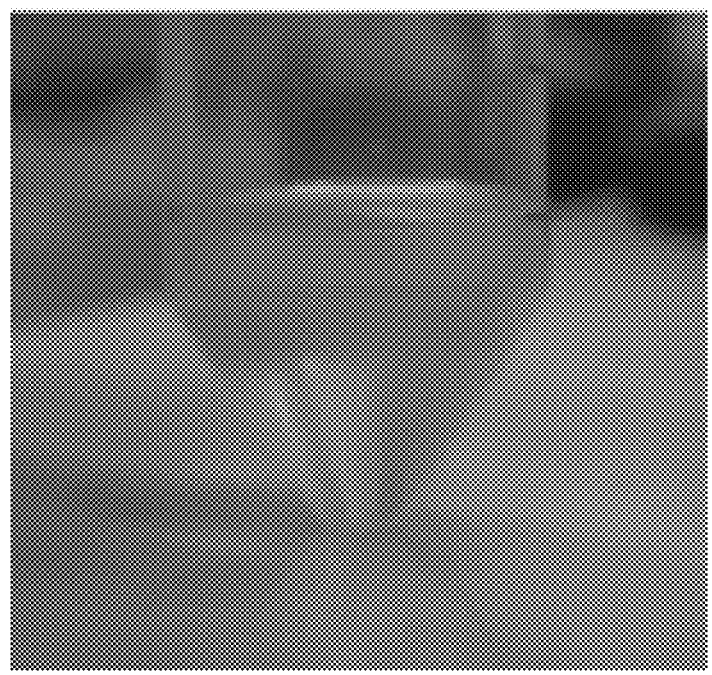
FIGS. 2A and 2B present a photograph of a 2.5% nanocrystalline cellulose suspension (FIG. 2A) and a tunneling electron microscope image showing cellulose nano-rods in the suspension (FIG. 2B) (scale bar in FIG. 2B indicates 500 nm)

The present invention, in some embodiments thereof, relates to the field of polymeric materials, and, more particularly, but not exclusively, to materials comprising elastic biopolymers and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While studying the properties of resilin polypeptides, the present inventors have uncovered that resilient, biocompatible and homogeneous compositions-of-matter may be readily obtained by cross-linking resilin polypeptides with a polymeric substance comprising amine groups, using carbodiimide chemistry, rather than by cross-linking resilin polypeptides to one another via tyrosine residues as in naturally occurring resilin. Such compositions-of-matter may further be bound to an additional substance (e.g., an additional polymeric substance) to form a composite material which combines the resilience of the composition-of-matter with mechanical properties of the additional substance.

Referring now to the drawings, FIG. 1 shows an encoding DNA sequence and a protein sequence for a resilin polypeptide comprising a cellulose-binding domain, which facilitates binding of a composition-of-matter comprising the resilin polypeptide to cellulose.

Figure 2B:
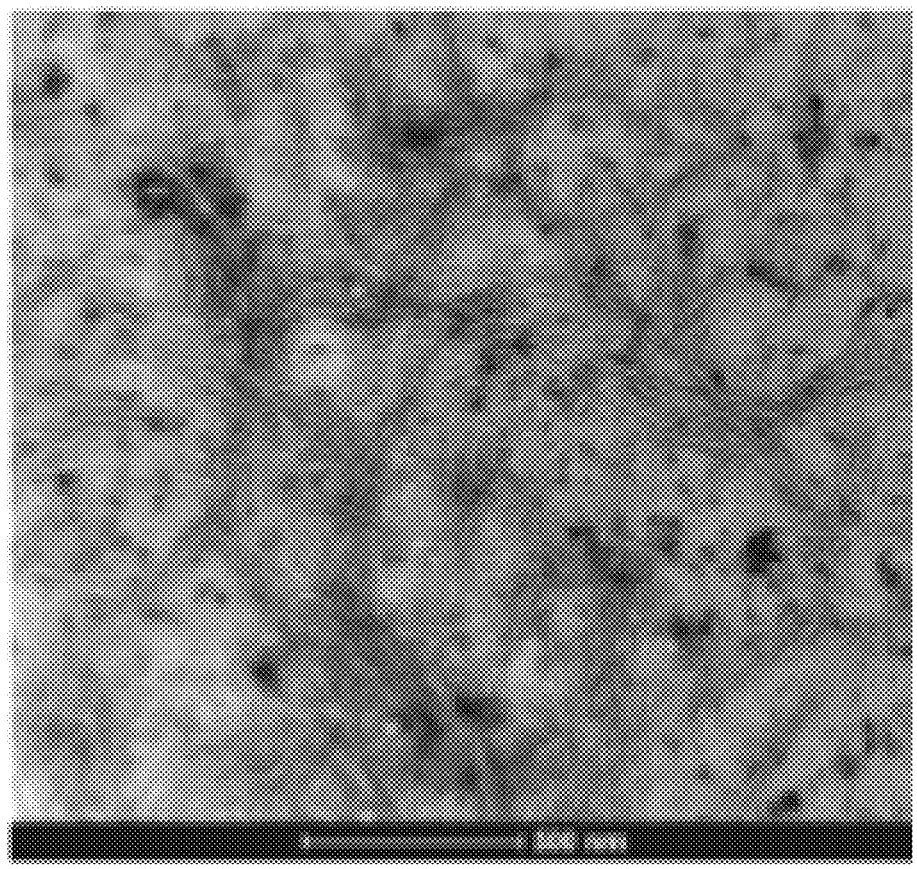
Figure 3A:
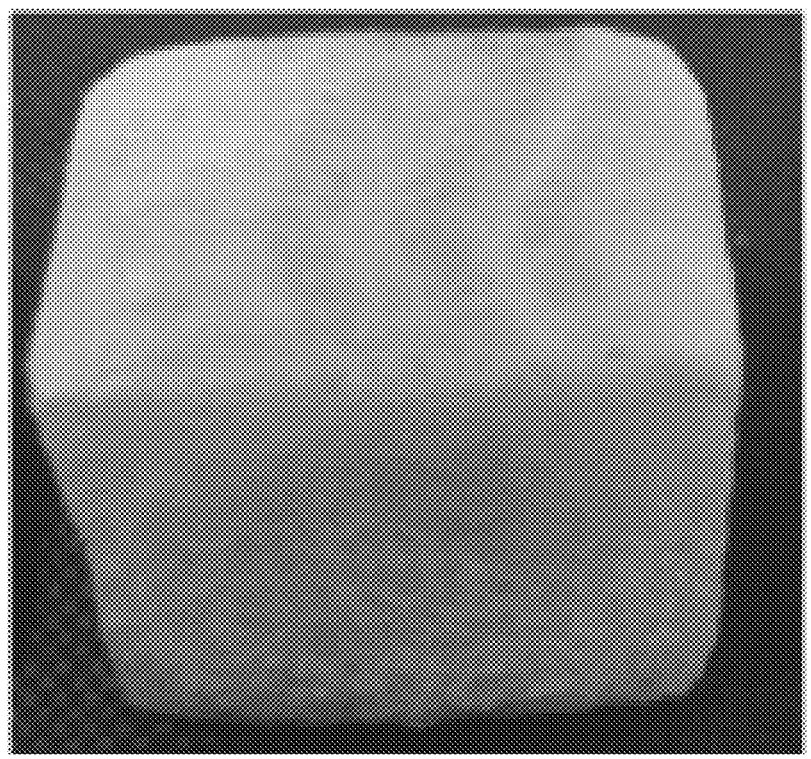
FIGS. 3A and 3B present a photograph of a nanocrystalline cellulose foam (FIG. 3A) and a scanning electron microscope image showing the nanostructure of the foam (FIG. 3B) (scale bar in FIG. 3B indicates 200 μm)
Figure 3B:
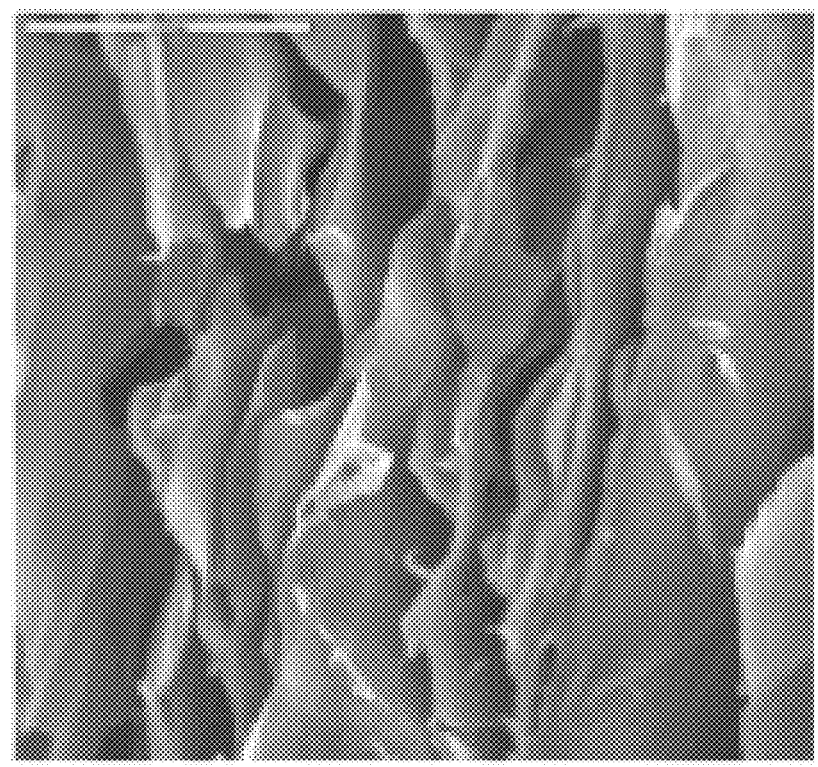

FIGS. 2A and 2B show a nanocrystalline cellulose suspension, and FIGS. 3A-3B show a nanocrystalline cellulose sponge (each without a resilin polypeptide).

Figure 4:
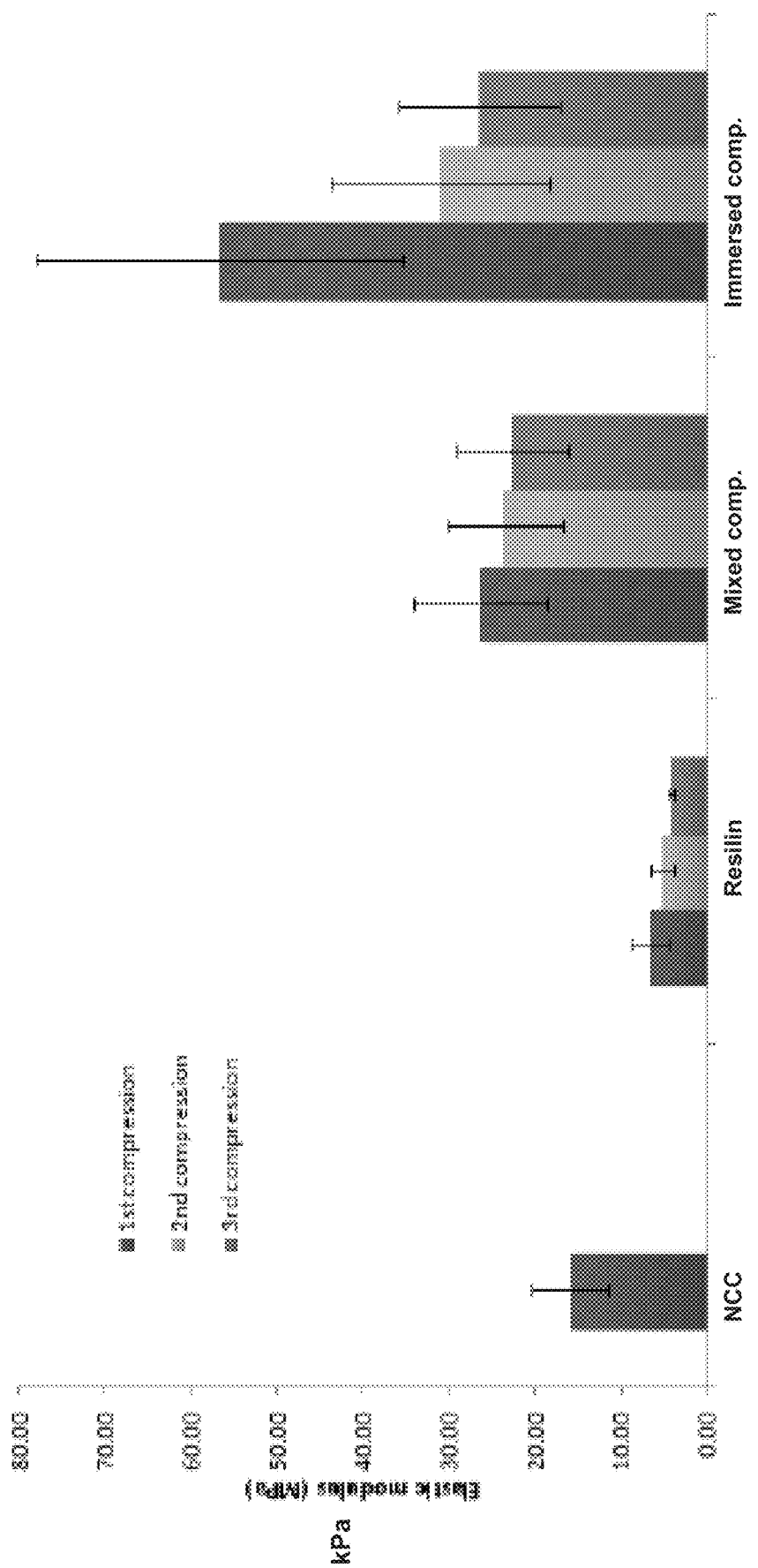
FIG. 4 is a bar graph showing the elastic modulus (y-axis) under compression of exemplary nanocrystalline cellulose (NCC) foam, resilin foam, resilin-NCC mixed composite foam, and resilin-NCC immersed composite foam (prepared as described herein) during a first, second and third cycle of compression.
Figure 5A:
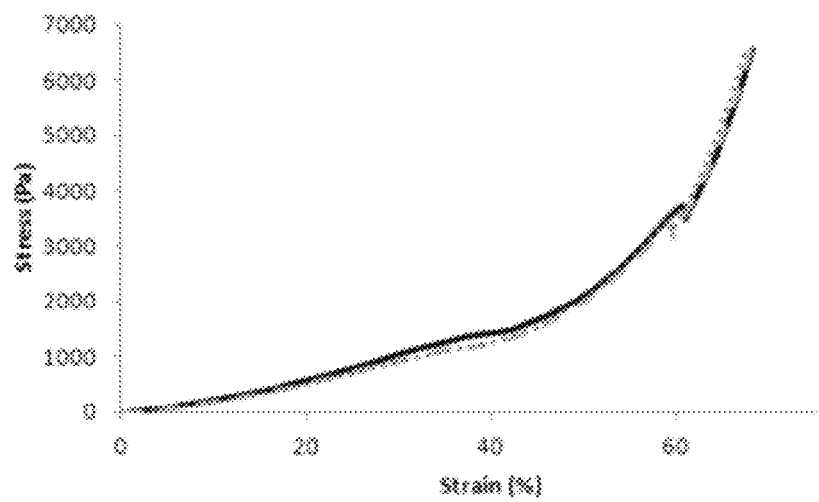
FIGS. 5A-5C are graphs showing the stress/strain curve under compression of an exemplary resilin foam (FIG. 5A), resilin-NCC mixed composite foam (FIG. 5B), and resilin-NCC immersed composite foam (FIG. 5C) during a first (solid line), second (dashed line) and third (dotted line) cycle of compression.
Figure 5B:
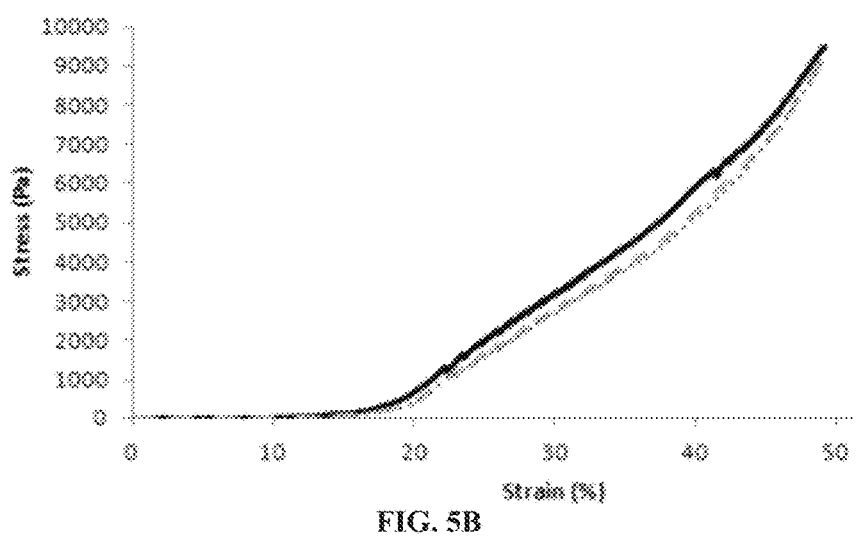
Figure 5C:
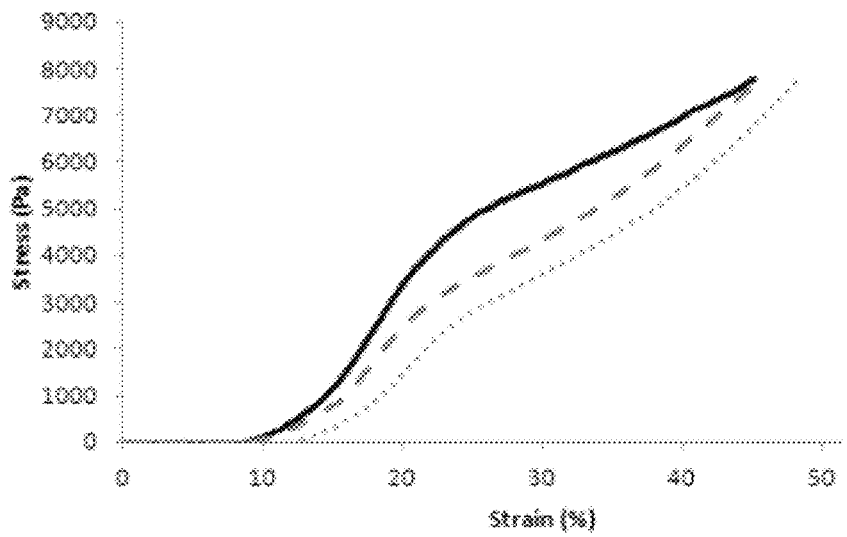
Figure 6:
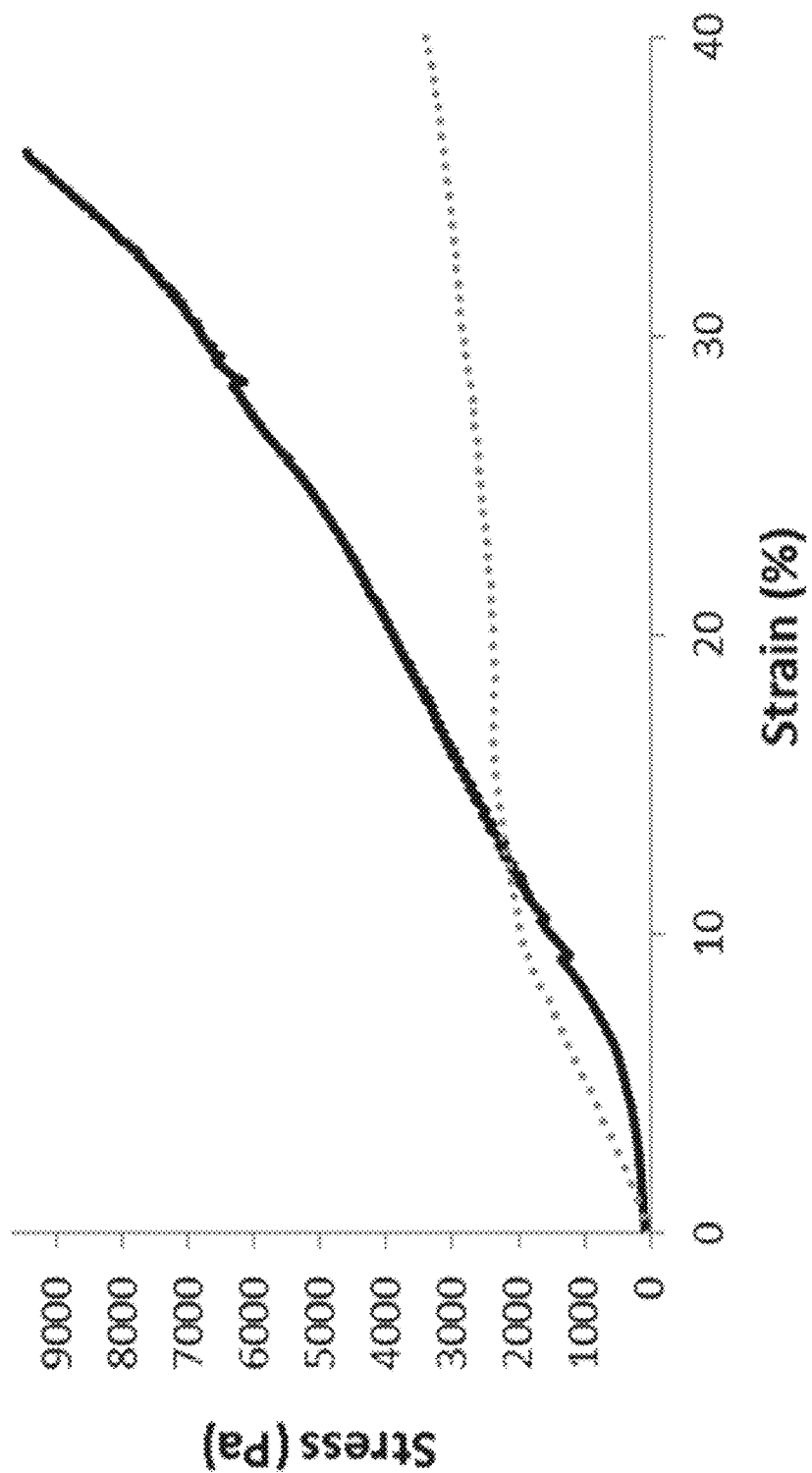
FIG. 6 is a graph showing the stress/strain curve under compression of an exemplary resilin-NCC foam (solid line) and NCC foam (dotted line)

FIG. 4 shows the resilience of exemplary cross-linked resilin polypeptide sponges and cross-linked resilin polypeptide-nanocrystalline cellulose composite sponges under compression, as compared with nanocrystalline cellulose sponges. FIGS. 4-6 further show the enhanced mechanical strength of the cross-linked resilin polypeptide-nanocrystalline cellulose composite sponges, as compared with cross-linked resilin polypeptide sponges and nanocrystalline cellulose sponges.

Figure 7:
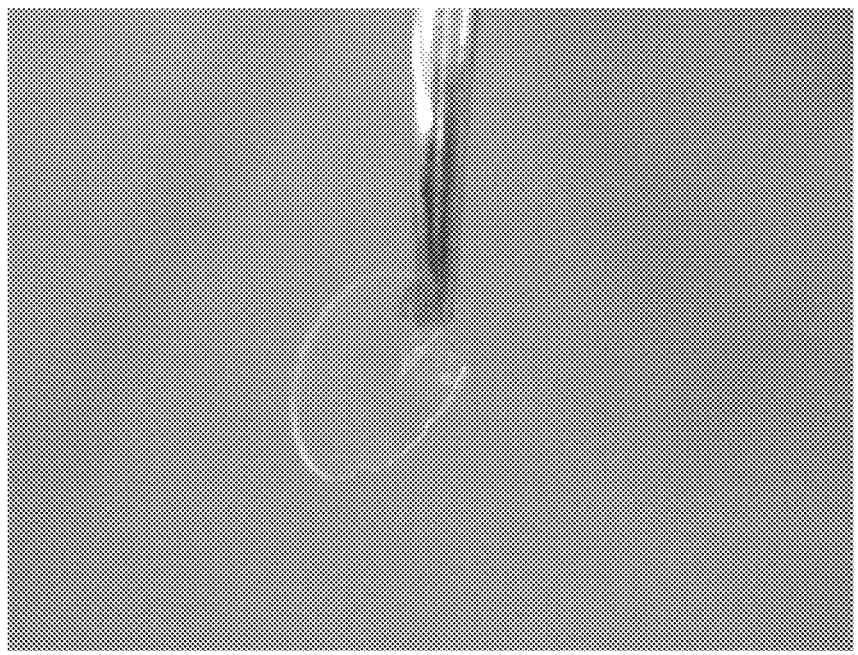
FIG. 7 presents an optical image of an exemplary cross-linked resilin membrane according to some embodiments of the invention.
Figure 8:
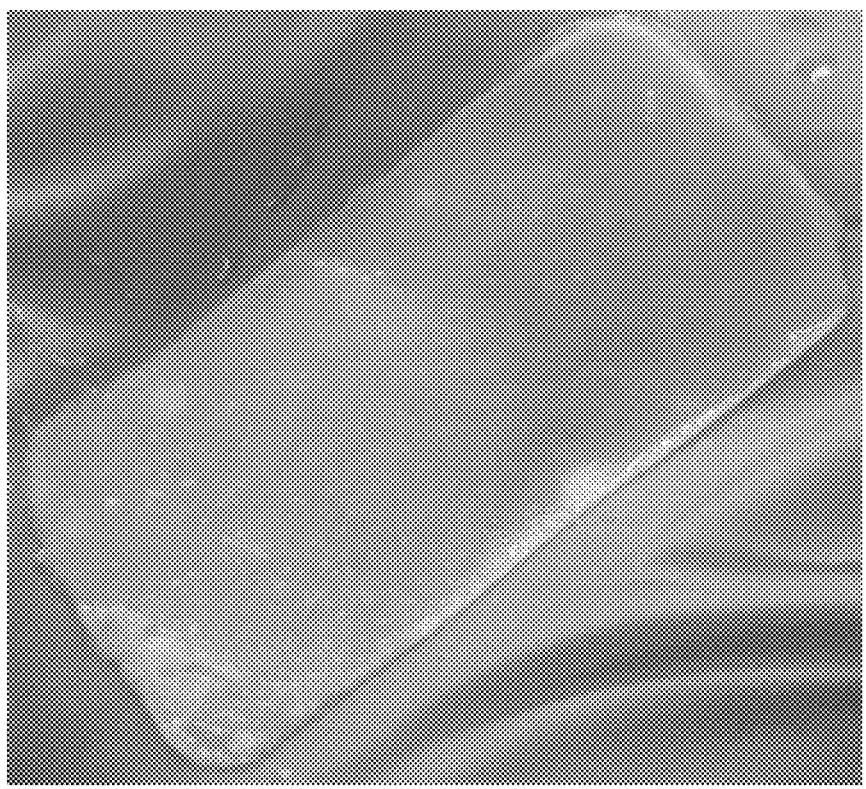
FIG. 8 presents an optical image of an exemplary cross-linked collagen-resilin membrane according to some embodiments of the invention.

FIGS. 7 and 8 show images of an exemplary cross-linked resilin polypeptide in a form of a membrane.

Figure 9:
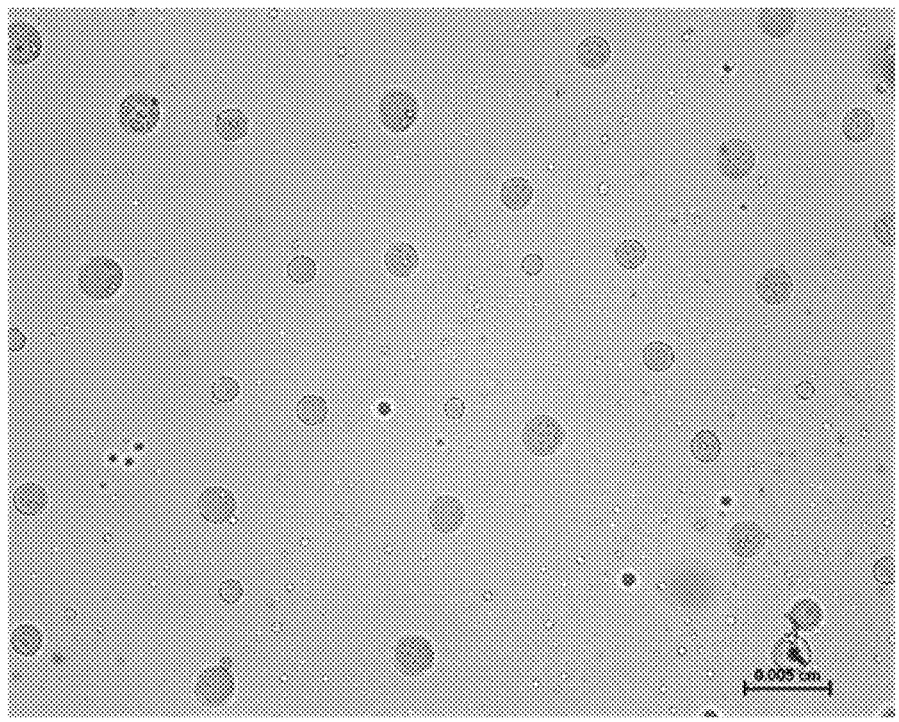
FIG. 9 presents an optical microscopic image of exemplary non-cross-linked resilin spheres prepared according to some embodiments of the invention (the diameter of the spheres ranges from about 10-20 μm; the scale bar represents 500 μm)
Figure 10:
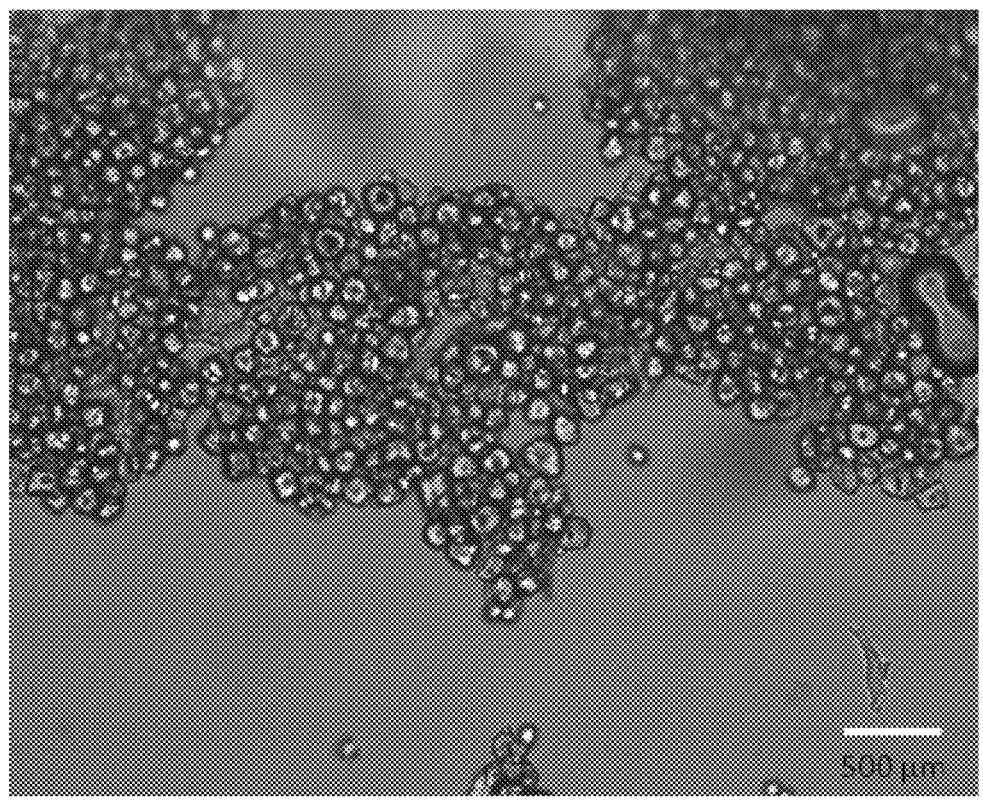
FIG. 10 presents an optical microscopic image of exemplary cross-linked resilin spheres according to some embodiments of the invention (the scale bar represents 500 μm).

FIGS. 9 and 10 show exemplary resilin polypeptide spheres prior to (FIG. 9) and subsequent to (FIG. 10) cross-linking of the resilin polypeptide. The cross-linked resilin polypeptide spheres may be used, for example to form a composite material by being bound to an additional substance.

According to an aspect of embodiments of the invention, there is provided a composition-of-matter comprising a cross-linked polymer. The cross-linked polymer comprises a plurality of resilin polypeptide moieties and at least one polymeric moiety covalently cross-linked to the plurality of the resilin polypeptide moieties via at least one cross-linking moiety.

Thus, the composition-of-matter comprises at least one polymeric moiety which is cross-linked with a plurality of resilin polypeptide moieties, thereby cross-linking the plurality of resilin polypeptide moieties. In some of any of the embodiments described herein, the composition-of-matter further comprises at least one polymeric moiety covalently cross-linked with a single resilin polypeptide moiety, but does not link a plurality of resilin polypeptide moieties together.

In some of any of the embodiments described herein, at least a portion of the resilin polypeptide moieties are covalently cross-linked with a plurality of polymeric moieties, thereby forming a covalently cross-linked three-dimensional network comprising a plurality of resilin polypeptide moieties and a plurality of polymeric moieties.

In some of any of the embodiments described herein, the composition-of-matter comprises a scaffold comprising cross-linked resilin polypeptide moieties and polymeric moieties.

As used herein, the term "scaffold" describes a two-dimensional or a three-dimensional supporting framework. The scaffold according to embodiments of the present invention is composed of units comprising moieties as described herein (e.g., polymeric moieties and resilin polypeptide moieties, as described herein) which are cross-linked therebetween.

Without being bound by any particular theory, it is believed that cross-linking of resilin polypeptide moieties with a substantial amount of polymeric moieties, as described herein, surprisingly provides the composition-of-matter with considerable mechanical strength over macroscopic distances, without substantially sacrificing the resilience associated with resilin. Consequently, a composition-of-matter characterized by considerable resilience can surprisingly and advantageously be obtained from resilin without requiring direct cross-linking of resilin polypeptides with each other (i.e., without addition of a polymeric substance, as described previously in the art), which may be technically difficult and/or fail to provide a desired mechanical strength.

In some of any of the embodiments described herein, at least 10 weight percents (of the dry weight) of the cross-linked polymer is the polymeric moiety. In some embodiments, at least 20 weight percents of the cross-linked polymer is the polymeric moiety. In some embodiments, at least 30 weight percents of the cross-linked polymer is the polymeric moiety. In some embodiments, at least 40 weight percents of the cross-linked polymer is the polymeric moiety. In some embodiments, at least 50 weight percents of the cross-linked polymer is the polymeric moiety. In some embodiments, at least 60 weight percents of the cross-linked polymer is the polymeric moiety. In some embodiments, at least 70 weight percents of the cross-linked polymer is the polymeric moiety. In some embodiments, at least 80 weight percents of the cross-linked polymer is the polymeric moiety. In some embodiments, at least 90 weight percents of the cross-linked polymer is the polymeric moiety.

In some of any of the embodiments described herein, at least 10 weight percents (of the dry weight) of the cross-linked polymer is the resilin polypeptide moiety. In some embodiments, at least 20 weight percents of the cross-linked polymer is the resilin polypeptide moiety. In some embodiments, at least 30 weight percents of the cross-linked polymer is the resilin polypeptide moiety. In some embodiments, at least 40 weight percents of the cross-linked polymer is the resilin polypeptide moiety. In some embodiments, at least 50 weight percents of the cross-linked polymer is the resilin polypeptide moiety. In some embodiments, at least 60 weight percents of the cross-linked polymer is the resilin polypeptide moiety. In some embodiments, at least 70 weight percents of the cross-linked polymer is the resilin polypeptide moiety. In some embodiments, at least 80 weight percents of the cross-linked polymer is the resilin polypeptide moiety.

In some of any of the embodiments described herein, the total weight of the resilin polypeptide moieties and polymeric moieties represents at least 50 weight percents of the dry weight of the cross-linked polymer. In some embodiments, the total weight of the resilin polypeptide moieties and polymeric moieties represents at least 60 weight percents of the dry weight of the cross-linked polymer. In some embodiments, the total weight of the resilin polypeptide moieties and polymeric moieties represents at least 70 weight percents of the dry weight of the cross-linked polymer. In some embodiments, the total weight of the resilin polypeptide moieties and polymeric moieties represents at least 80 weight percents of the dry weight of the cross-linked polymer. In some embodiments, the total weight of the resilin polypeptide moieties and polymeric moieties represents at least 90 weight percents of the dry weight of the cross-linked polymer. In some embodiments, the total weight of the resilin polypeptide moieties and polymeric moieties represents at least 95 weight percents of the dry weight of the cross-linked polymer. In some embodiments, the total weight of the resilin polypeptide moieties and polymeric moieties represents at least 99 weight percents of the dry weight of the cross-linked polymer.

Herein, the phrases "resilin polypeptide" and "resilin polypeptide moiety" encompass a polypeptide comprising a sequence of a resilin protein, a fragment of a resilin protein, or a homologous polypeptide thereof (i.e., a polypeptide homologous to a resilin protein or fragment thereof, as defined herein). The phrase "resilin polypeptide moiety" refers to a moiety that forms a part of a molecule, whereas the phrase "resilin polypeptide" may refer to both a molecule per se or a moiety that forms a part of the molecule.

Herein, a "homologous polypeptide" of a given polypeptide encompasses polypeptides which are at least 50%, at least 55%, at least 60%, at least 65%, at least 70%, at least 75%, at least 80%, at least 85%, at least 87%, at least 89%, at least 91%, at least 93%, at least 95% or more, e.g., 100%, homologous to the given polypeptide, such as a resilin polypeptide described herein (e.g., a sequence listed in Table 1 or a fragment thereof), as determined using BlastP software of the National Center of Biotechnology Information (NCBI) using default parameters. The homologous polypeptide may also refer to a deletion, insertion, or substitution variant, including an amino acid substitution, thereof and biologically active polypeptide fragments thereof.

In some of any of the embodiments described herein, a homologous polypeptide is at least 80% homologous, as defined hereinabove. In some embodiments, a homologous polypeptide is at least 85% homologous, as defined hereinabove. In some embodiments, a homologous polypeptide is at least 90% homologous, as defined hereinabove. In some embodiments, a homologous polypeptide is at least 95% homologous, as defined hereinabove. In some embodiments, a homologous polypeptide is at least 98% homologous, as defined hereinabove. In some embodiments, a homologous polypeptide is at least 99% homologous, as defined hereinabove.

In some of any of the embodiments described herein, a fragment of a resilin protein (or homologous polypeptide thereof) is at least 50 amino acid residues in length. In some embodiments, a fragment of a resilin protein is at least 60 amino acid residues in length. In some embodiments, a fragment of a resilin protein is at least 70 amino acid residues in length. In some embodiments, a fragment of a resilin protein is at least 80 amino acid residues in length. In some embodiments, a fragment of a resilin protein is at least 100 amino acid residues in length. In some embodiments, a fragment of a resilin protein is at least 125 amino acid residues in length. In some embodiments, a fragment of a resilin protein is at least 150 amino acid residues in length. In some embodiments, a fragment of a resilin protein is at least 200 amino acid residues in length.

In some of any of the embodiments described herein, the resilin polypeptide moiety consists essentially of resilin, a fragment thereof, or a homologous polypeptide thereof.

In some of any of the embodiments described herein, the resilin polypeptide moiety comprises one or more peptide sequence(s) in addition to resilin, a fragment thereof, or a homologous polypeptide thereof.

GenBank Accession Nos. of non-limiting examples of resilin are listed in Table 1 below.

TABLE 1

| Exemplary resilin NCBI sequence number | Organism |
| --- | --- |
| NP 995860 | Drosophila melanogaster |
| NP 611157 | Drosophila melanogaster |
| Q9V7U0 | Drosophila melanogaster |
| AAS64829 | Drosophila melanogaster |
| AAF57953 | Drosophila melanogaster |
| XP 001817028 | Tribolium castaneum |
| XP001947408 | Acyrthosiphon pisum |

According to some of any of the embodiments described herein, the resilin polypeptide moiety comprises the full length resilin amino acid sequence (i.e. comprises amino acids from each of exon 1, exon 2 and exon 3), for example, as set forth in SEQ ID NO: 19.

According to other embodiments, the resilin polypeptide moiety comprises an exon 1 resilin amino acid sequence (SEQ ID NOs: 1, 2 or 16), or a homologous polypeptide sequence, which may be 70% homologous, 75% homologous, 80% homologous, 85% homologous, 90% homologous, 91% homologous, 92% homologous, 93% homologous, 94% homologous, 95% homologous, 96% homologous, 97% homologous, 98% homologous, 99% homologous or 100% homologous to the sequence as set forth in SEQ ID NOs: 1, 2 or 16 as determined using BlastP software of the National Center of Biotechnology Information (NCBI) using default parameters). The homologous polypeptide sequence may also refer to a deletion, insertion, or substitution variant, including an amino acid substitution, thereof and biologically active polypeptide fragments thereof.

In some of any of the embodiments described herein, the resilin amino acid sequence comprises an exon 1 resilin amino acid sequence and a polysaccharide binding domain (e.g. a cellulose binding domain (CBD) and/or a chitin binding domain (ChBD), such as that encoded in exon 2).

Herein, the phrase "polysaccharide-binding domain" refers to a polypeptide or a portion thereof which is capable of selectively binding to a polysaccharide. Various polysaccharide-binding domains are known in the art.

An example of a ChBD sequence found in exon 2 of resilin is provided in SEQ ID NO: 3 or 6.

Examples of cellulose binding domain (CBD) amino acid sequences are provided in SEQ ID NOs: 17 and 18.

Additional polysaccharide binding domains are provided in International Patent Application Publication No. WO2009/069123, incorporated herein by reference.

The polysaccharide binding domain may be linked to the C terminal domain of exon 1 or the N terminal domain of exon 1 (either directly or via a linker).

An exemplary exon 1 resilin amino acid sequences linked to a cellulose binding domain is provided in FIG. 1.

According to still other embodiments, the resilin polypeptide moiety amino acid sequence comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating units as set forth in SEQ ID NO: 4 (Gly Gly Arg Pro Ser Asp Ser Tyr Gly Ala Pro Gly Gly Gly Asn).

According to still other embodiments the resilin polypeptide moiety amino acid sequence comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating units as set forth in SEQ ID NO: 5 (GRPSDSYGA).

According to still other embodiments the resilin amino acid sequence is devoid of an exon 3 amino acid sequence.

According to yet other embodiments, the resilin amino acid sequence comprises an exon 3 amino acid sequence.

Examples of polynucleotides which can be used to express resilin are set forth in SEQ ID NO: 7, 8, 10, 12 and 14.

Examples of 6H-tagged resilin polypeptide sequences are set forth in SEQ ID NO: 9, 11, 13 and 15. SEQ ID NO: 13 is an exemplary polypeptide sequence. Such sequences may be readily isolated utilizing the 6H-tag, and may be incorporated as is in the composition-of-matter or incorporated after removing the 6H-tag, as exemplified herein.

Other exemplary polypeptide and polynucleotide sequences that may be used are provided in International Application No. WO 2009/069123 and in International Patent Application No. PCT/IL2012/050340, which are incorporated herein by reference.

The term "polypeptide" as used herein encompasses native peptide macromolecules (e.g., a resilin polypeptide), including degradation products, synthetically prepared peptides and recombinant peptides (e.g., recombinantly expressed in a microorganism), as well as peptidomimetic macromolecules (typically, synthetically synthesized peptides), as well as peptoid and semipeptoid macromolecules which are peptide analogs, which may have, for example, modifications rendering the polypeptides more stable. Such modifications include, but are not limited to N-terminus modification, C-terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein below.

Peptide bonds (—CO—NH—) within the polypeptide may be substituted, for example, by N-methylated amide bonds (—N(CH3)-CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g. methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), retro-amide bonds (—NH—CO—), peptide derivatives (—N(R)—CH$_2$—CO—), wherein R is the "normal" side chain, naturally present on the carbon atom.

These modifications can occur at any of the bonds along the polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The polypeptides of some of any of the embodiments described herein may also include one or more modified amino acids or one or more non-amino acid monomers e.g. fatty acids, complex carbohydrates etc.

The term "amino acid" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids e.g. synthetic (Table 3) which can be used with some embodiments of the invention.

TABLE 2

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 3

| Non-conventional amino acid | Code | Non-conventional amino acid | Code |
| --- | --- | --- | --- |
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |

TABLE 3-continued

| Non-conventional amino acid | Code | Non-conventional amino acid | Code |
|---|---|---|---|
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |

TABLE 3-continued

| Non-conventional amino acid | Code | Non-conventional amino acid | Code |
| --- | --- | --- | --- |
| phosphoserine | pSer | phosphothreonine | pThr |
| phosphotyrosine | pTyr | O-methyl-tyrosine | |
| 2-aminoadipic acid | | hydroxylysine | |

The polypeptides of some embodiments of the invention are preferably utilized in a linear form, although it will be appreciated that in cases where cyclization does not severely interfere with polypeptide characteristics, cyclic forms of the polypeptide can also be utilized.

The polypeptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after de-protection, a pentapeptide and so forth. Further description of polypeptide synthesis is disclosed in U.S. Pat. No. 6,472,505.

A preferred method of preparing a polypeptide some embodiments of the invention involves solid phase polypeptide synthesis.

Large scale polypeptide synthesis is described by Andersson [*Biopolymers* 2000; 55(3):227-50].

Polynucleotides of the present invention may be prepared using PCR techniques as described in the Examples section below, or can be chemically synthesized or by any other method or procedure known in the art for ligation of two different DNA sequences. See, for example, "Current Protocols in Molecular Biology", eds. Ausubel et al., John Wiley & Sons, 1992.

Polypeptides of the present invention can be purified using a variety of standard protein purification techniques, such as, but not limited to, heat treatments, salting out for example with ammonium sulfate, polyethyleneimines (PEI) precipitation, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety (see Examples section, herein below).

Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in a "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Following expression and optional purification of the polypeptides of the present invention, the polypeptides may be cross-linked (e.g., as described herein) to form an insoluble material from a solution, preferably one with a relatively high concentration of polypeptide. According to one embodiment, the critical concentration of a resilin polypeptide of the present invention is about 50 mg/ml. According to one embodiment, the polypeptide is concentrated by ultracentrifugation.

In some of any of the embodiments described herein, the polymeric moiety described herein comprises a polypeptide, as defined herein.

In exemplary embodiments, the polymeric moiety comprises collagen (e.g., human recombinant collagen, a fragment of collagen, or a polypeptide homologous to collagen or a fragment thereof, as defined herein).

In some of any of the embodiments described herein, a fragment of collagen (or homologous polypeptide thereof) is at least 50 amino acid residues in length. In some embodiments, a fragment of collagen is at least 60 amino acid residues in length. In some embodiments, a fragment of collagen is at least 70 amino acid residues in length. In some embodiments, a fragment of collagen is at least 80 amino acid residues in length. In some embodiments, a fragment of collagen is at least 100 amino acid residues in length. In some embodiments, a fragment of collagen is at least 125 amino acid residues in length. In some embodiments, a fragment of collagen is at least 150 amino acid residues in length. In some embodiments, a fragment of collagen is at least 200 amino acid residues in length.

In some of any of the embodiments described herein, the polymeric moiety described herein comprises a synthetic or semi-synthetic polymer. Examples of synthetic and semi-synthetic polymers which may be used in embodiments of the invention include, without limitation, polyalkylene glycols; poly(ethylene-co-vinyl alcohol); poly(hydroxyvalerate); poly(lactic acid); polycaprolactone; poly(lactide-co-glycolide); poly(hydroxybutyrate); poly(hydroxybutyrate-co-valerate); polydioxanone; polyesters; polyanhydrides; poly(glycolic acid); poly(glycolic acid-co-trimethylene carbonate); polycyanoacrylates; poly(trimethylene carbonate); poly(iminocarbonate); polyalkylene oxalates; polyphosphazenes; polyurethanes; silicones; polyolefins (e.g., polyethylene, polypropylene); polyacrylates and polymethacrylates; polyacrylamides and polymethacrylamides; vinyl halide polymers (e.g., polyvinyl chloride); polyvinyl ethers (e.g., polyvinyl methyl ether); polyvinylidene halides (e.g., polyvinylidene fluoride and polyvinylidene chloride); polyacrylonitrile; polyvinyl ketones; polyvinyl aromatics (e.g., polystyrene); polyvinyl esters (e.g., polyvinyl acetate); polyamides (e.g., Nylon 66 and other nylons, polycaprolactam); polycarbonates; polyoxymethylenes; polyimides; polyethers; cellulose and cellulose-derived polymers (e.g., rayon, rayon triacetate, cellulose acetate, cellulose butyrate, cellulose acetate butyrate, cellulose nitrate, cellulose propionate, cellulose ethers, carboxymethyl cellulose); and co-polymers thereof.

In some of any of the embodiments described herein, the polymeric moiety is hydrophilic (e.g., swellable in water).

In some of any of the embodiments described herein, the polymeric moiety comprises a polyalkylene glycol.

The phrase "poly(alkylene glycol)", as used herein, encompasses a family of polyether polymers which share the following general formula: —O—[(CH$_2$)m-O-]n-, wherein m represents the number of methylene groups present in each alkylene glycol unit, and n represents the number of repeating units, and therefore represents the size or length of the polymer. For example, when m=2, the polymer is referred to as a polyethylene glycol, and when m=3, the polymer is referred to as a polypropylene glycol.

In some of any of the embodiments described herein, m is an integer greater than 1 (e.g., m=2, 3, 4, etc.).

Optionally, m varies among the units of the poly(alkylene glycol) chain. For example, a poly(alkylene glycol) chain may comprise both ethylene glycol (m=2) and propylene glycol (m=3) units linked together.

The phrase "poly(alkylene glycol)" also encompasses analogs thereof, in which the oxygen atom is replaced by another heteroatom such as, for example, S, —NH— and the like. This term further encompasses derivatives of the above, in which one or more of the methylene groups composing the polymer are substituted. Exemplary substituents on the methylene groups include, but are not limited to, alkyl, cycloalkyl, alkoxy, hydroxy, thiol, amine, halo, oxo, carbonyl, carboxylate, carbamate, and the like.

Thus, the phrase "alkylene glycol unit", as used herein, encompasses a —(CH$_2$)m-O— group or an analog thereof, as described hereinabove, which forms the backbone chain of the poly(alkylene glycol), wherein the (CH$_2$)m (or analog thereof) is bound to a heteroatom belonging to another alkylene glycol unit and/or to a cross-linking moiety.

An alkylene glycol unit may be branched, such that it is linked to 3 or more neighboring alkylene glycol units, wherein each of the 3 or more neighboring alkylene glycol units are part of a poly(alkylene glycol) chain. Such a branched alkylene glycol unit is linked via the heteroatom thereof to one neighboring alkylene glycol unit, and heteroatoms of the remaining neighboring alkylene glycol units are each linked to a carbon atom of the branched alkylene glycol unit. In addition, a heteroatom (e.g., nitrogen) may bind more than one carbon atom of an alkylene glycol unit of which it is part, thereby forming a branched alkylene glycol unit (e.g., [(—CH$_2$)m]$_2$N— and the like).

The terminal heteroatoms (e.g., an oxygen atom) of an poly(alkylene glycol) group are bound to an atom which may be, for example, a hydrogen atom, an atom in a neighboring moiety (e.g., a polypeptide described herein) or an atom (e.g., a carbon atom) of an end group. The end group may be a relatively inert "cap", such as an alkyl group (e.g., non-substituted alkyl), or a more reactive group (e.g., a group containing amine), for example, a group which reacts with a neighboring moiety (e.g., a moiety described herein) to thereby link the poly(alkylene glycol) to the neighboring moiety.

In exemplary embodiments, at least 50% of alkylene glycol units are identical, e.g., they comprise the same heteroatoms and the same m values as one another. Optionally, at least 70%, optionally at least 90%, and optionally 100% of the alkylene glycol units are identical. In exemplary embodiments, the heteroatoms bound to the identical alkylene glycol units are oxygen atoms. In further exemplary embodiments, m is 2 for the identical units.

In some of any of the embodiments described herein, the poly(alkylene glycol) is a poly(ethylene glycol) (PEG).

As used herein, the term "poly(ethylene glycol)" describes a poly(alkylene glycol), as defined hereinabove, wherein at least 50%, at least 70%, at least 90%, and preferably 100%, of the alkylene glycol units are —CH$_2$CH$_2$—O—. Similarly, the phrase "ethylene glycol units" is defined herein as units of —CH$_2$CH$_2$O—.

In some of any of the embodiments described herein, the polymeric moiety is linear, that is, it comprises a single, straight chain as backbone.

In some of any of the embodiments described herein, the polymeric moiety comprises branched chains, also known as multi-antennary. In some embodiments, each branched chain is linked to a resilin polypeptide moiety via a cross-linking moiety. In some embodiments, the polymeric moiety comprises branched PEG (e.g., "star PEG"). 8-arm PEG is an exemplary branched PEG.

In some of any of the embodiments described herein, the polymeric moiety has a molecular weight of at least about 2 kDa. In some embodiments, the polymeric moiety has a molecular weight of at least about 3 kDa. In some embodiments, the polymeric moiety has a molecular weight of at least about 4 kDa. In some embodiments, the polymeric moiety has a molecular weight of at least about 5 kDa. In some embodiments, the polymeric moiety has a molecular weight of at least about 6 kDa. In some embodiments, the polymeric moiety has a molecular weight of at least about 7 kDa. In some embodiments, the polymeric moiety has a molecular weight of at least about 8 kDa. In some embodiments, the polymeric moiety has a molecular weight of at least about 9 kDa. In exemplary embodiments, the polymeric moiety has a molecular weight of at least about 10 kDa.

In some of any of the embodiments described herein, the polymeric moiety comprises terminal amine groups, such as amine-terminated PEG. Amine-terminated PEG is also referred to herein as "PEG-amine".

In some of any of the embodiments described herein, the polymeric moiety comprises a branched amine-terminated polymer (e.g., branched PEG-amine). Such a polymer may comprise a terminal amine group on all of the branches, or on only a portion of the branches. In some embodiments, branched amine-terminated polymer comprises at least 3 terminal amine groups. In some embodiments, branched amine-terminated polymer comprises at least 4 terminal amine groups. In some embodiments, branched amine-terminated polymer comprises at least 6 terminal amine groups. In some embodiments, branched amine-terminated polymer comprises at least 8 terminal amine groups.

8-arm PEG-amine, comprising terminal 8 amine groups, is an exemplary branched amine-terminated polymer.

In some of any of the embodiments described herein, the cross-linking moieties described herein, which cross-link a resilin polypeptide moiety with a polymeric moiety, are moieties devoid of a biphenyl moiety.

Herein, a "biphenyl moiety" refers to any moiety having the formula:

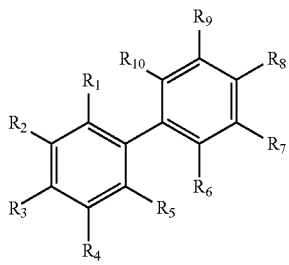

wherein each of $R_1$-$R_{10}$ is independently hydrogen or any substituent, or a covalent bond with a resilin polypeptide moiety or polymeric moiety as described herein (e.g., moieties being cross-linked by the biphenyl moiety), wherein at least one of $R_1$-$R_5$ is a covalent bond with a resilin polypeptide moiety or polymeric moiety, and at least one of $R_6$-$R_{10}$ is a covalent bond with a resilin polypeptide moiety or polymeric moiety.

In some of any of the embodiments described herein, the composition-of-matter is substantially devoid of biphenyl moieties.

In some of any of the embodiments described herein, the composition-of-matter is substantially devoid of biphenyl moieties formed by a bond between two hydroxyphenyl groups (e.g., a bond between two tyrosine residues), such that at least one of $R_1$-$R_5$ and at least one of $R_6$-$R_{10}$ is hydroxy (i.e., —OH).

In some of any of the embodiments described herein, the composition-of-matter is substantially devoid of biphenyl moieties formed by a bond between two dihydroxyphenyl groups (e.g., a bond between two DOPA residues), such that at least two of $R_1$-$R_5$ and at least two of $R_6$-$R_{10}$ are hydroxy.

Herein, the phrase "substantially devoid of" means that there is no more than one biphenyl moiety (as described herein) per 20 kDa of cross-linked polymer. In some embodiments, there is no more than one biphenyl moiety per 40 kDa of cross-linked polymer. In some embodiments, there is no more than one biphenyl moiety per 60 kDa of cross-linked polymer. In some embodiments, there is no more than one biphenyl moiety per 80 kDa of cross-linked polymer. In some embodiments, there is no more than one biphenyl moiety per 100 kDa of cross-linked polymer. In some embodiments, there is no more than one biphenyl moiety per 150 kDa of cross-linked polymer. In some embodiments, there is no more than one biphenyl moiety per 200 kDa of cross-linked polymer.

Detection and quantification of biphenyl moieties may be performed by hydrolysis of the polypeptide and analysis of amino acids, for example, in International Patent Application No. PCT/IL2012/050340.

In some of any of the embodiments described herein, the cross-linking moiety comprises an amide bond.

Herein, an "amide bond" refers to the bond between the C=O and the N(R') in a —C(=O)—N(R')— (i.e., amide) group, wherein R' is hydrogen, alkyl, cycloalkyl, heteroalicyclic, aryl or heteroaryl.

In exemplary embodiments, the cross-linking moiety is such that cleavage of the amide bond results in cleavage of the cross-link between the resilin polypeptide moiety and polymeric moiety described herein.

In some of any of the embodiments described herein, the cross-linking moiety comprises a residue of a cross-linking reagent attached to both the resilin polypeptide moiety and the polymeric moiety described herein.

In some of any of the embodiments described herein, the N(R') is formed from a part (e.g., an amine group) of the polymeric moiety.

In some of any of the embodiments described herein, the N(R') is formed from a part (e.g., an amine group) of the resilin polypeptide moiety.

In some of any of the embodiments described herein, the C=O is formed from a part (e.g., a carboxylic group) of the polymeric moiety.

In some of any of the embodiments described herein, the C=O is formed from a part (e.g., a carboxylic group) of the resilin polypeptide moiety.

In some of any of the embodiments described herein, the cross-linking moiety consists of the amide bond, that is, each of the C=O and the N(R') in the —C(=O)—N(R')— (i.e., amide) group is formed from a part of the resilin polypeptide moiety or the polymeric moiety, the resilin polypeptide moiety and polymeric moiety being directly attached to one another via the amide bond.

In some of any of the embodiments described herein, the amide bond is not within a backbone of a polypeptide chain, that is, the amide bond is not between a C-terminus of one amino acid sequence and an N-terminus of another amino acid sequence.

In exemplary embodiments, the N(R') is formed from a part of the polymeric moiety and the C=O is formed from a part of the resilin polypeptide moiety.

Without being bound by any particular theory it is believed that resilin polypeptide moiety sequences are commonly deficient in amine groups, and that provision of a polymeric moiety with amine groups available for forming amide bonds is particularly useful for cross-linking resilin polypeptide moieties.

Hence, in some of any of the embodiments described herein, the polymeric moiety comprises a plurality of amine groups. Such a polymeric moiety is capable of being bound to one or more resilin polypeptide moieties via a plurality of cross-linking moieties, each comprising an amide bond formed from an amine group of the polymeric moiety. In some embodiments, the cross-linking moieties consist of an amide bond between an amine group of the polymeric moiety and a carboxylic group of the resilin polypeptide moiety.

In some of any of the embodiments described herein, the amide bond is formed from a carboxylic group which is part of a side chain of an amino acid residue selected from the group consisting of a glutamate residue and an aspartate residue. In some embodiments, such an amino acid residue is a resilin polypeptide moiety residue.

In some of any of the embodiments described herein, the amide bond is formed from an amine group which is part of an amino acid residue, for example, a side chain of an amino acid residue (e.g., lysine residue side chain). In some embodiments, such an amino acid residue is a part of the polymeric moiety as described herein (e.g., a polymeric moiety comprising a polypeptide).

In some of any of the embodiments described herein, the amide bond is formed from an amine group which is part of a polymeric moiety having amine groups. In some embodiments, the polymeric moiety comprises a poly(alkylene glycol), such as a PEG, having amine groups. In some embodiments, the amine groups comprise terminal amine groups, as described herein.

In some of any of the embodiments described herein, the composition-of-matter is in a form of a plurality of particles. In some embodiments, a diameter of the particles (i.e., the largest distance between two opposite parallel lines tangent to the boundary of the particle) is in a range of from 1 to 200 μm. In some embodiments, the diameter of the particles is in a range of from 2 to 100 μm. In some embodiments, the diameter of the particles is in a range of from 4 to 50 μm. In some embodiments, the diameter of the particles is in a range of from 8 to 25 μm.

In some of any of the embodiments described herein, the particles are substantially spheroid.

Herein, the phrase "substantially spheroid" refers to a shape wherein the diameter (i.e., the largest distance between two opposite parallel lines tangent to the boundary) is no more than twice the width (i.e., the smallest distance between two opposite parallel lines tangent to the boundary). In some embodiments, the diameter is no more than 1.5 times the width. In some embodiments, the diameter is no more than 1.2 times the width. In some embodiments, the diameter is no more than 1.1 times the width.

In some of any of the embodiments described herein, the particles of are covalently cross-linked to one another. In some embodiments, the particles are covalently cross-linked via at least one cross-linking moiety as described herein.

In some of any of the embodiments described herein, the composition-of-matter is in a form of a membrane.

In some of any of the embodiments described herein, an area of the membrane is at least 1 cm$^2$. In some embodiments, an area of the membrane is at least 3 cm$^2$. In some embodiments, an area of the membrane is at least 10 cm$^2$. In some embodiments, an area of the membrane is at least 30 cm$^2$. In some embodiments, an area of the membrane is at least 100 cm$^2$.

In some of any of the embodiments described herein, an average thickness of the membrane is no more than 3 mm. In some embodiments, an average thickness of the membrane is no more than 2 mm. In some embodiments, an average thickness of the membrane is no more than 1 mm. In some embodiments, an average thickness of the membrane is no more than 0.5 mm. In some embodiments, an average thickness of the membrane is no more than 0.2 mm. In some embodiments, an average thickness of the membrane is no more than 0.1 mm.

In some of any of the embodiments described herein, an average thickness of the membrane is at least 0.01 mm. In some embodiments, an average thickness of the membrane is at least 0.03 mm. In some embodiments, an average thickness of the membrane is at least 0.1 mm. In some embodiments, an average thickness of the membrane is at least 0.2 mm. In some embodiments, an average thickness of the membrane is at least 0.5 mm. In some embodiments, an average thickness of the membrane is at least 1 mm.

In some of any of the embodiments described herein, the composition-of-matter is characterized by a tensile strength of at least 0.1 MPa. In some embodiments, the composition-of-matter is characterized by a tensile strength of at least 0.3 MPa. In some embodiments, the composition-of-matter is characterized by a tensile strength of at least 1 MPa. In some embodiments, the composition-of-matter is characterized by a tensile strength of at least 3 MPa. In some embodiments, the composition-of-matter is characterized by a tensile strength of at least 10 MPa. In some embodiments, the composition-of-matter is characterized by a tensile strength of at least 30 MPa. Any value higher than the above-indicated values is contemplated.

In some of any of the embodiments described herein, the composition-of-matter is characterized by a modulus of resilience of at least 1 MPa. In some embodiments, the composition-of-matter is characterized by a modulus of resilience of at least 2 MPa. In some embodiments, the composition-of-matter is characterized by a modulus of resilience of at least 3 MPa. In some embodiments, the composition-of-matter is characterized by a modulus of resilience of at least 4 MPa. In some embodiments, the composition-of-matter is characterized by a modulus of resilience of at least 5 MPa. Any value higher than the above-indicated values is contemplated.

Herein, mechanical properties refer to properties of the composition-of-matter following contact with an aqueous medium (e.g., water or 20 mM aqueous sodium phosphate (pH 7.5)), for example, in a composition-of-matter swollen with aqueous medium, when the degree of aqueous medium in the swollen composition-of-matter has stabilized (e.g., remained constant).

Without being bound by any particular theory, it is believed that the composition-of-matter, like resilin, is particularly elastic and resilient when swollen with a polar solvent (e.g., an aqueous solvent).

As exemplified herein, the cross-linked polymer of the composition-of-matter may be bound to a polymeric substance so as to form a composite material.

Hence, according to another aspect of embodiments of the invention, there is provided a composite material comprising a composition-of-matter as described herein, and at least one additional polymeric substance bound to the cross-linked polymer of the composition-of-matter.

Herein, a "composite material" refers to a material comprising two or more constituent materials (e.g., the composition-of-matter described herein, and an additional polymeric substance described herein), which remain separate and distinct within the composite material (e.g., present in separate regions of the composite material).

The additional polymeric substance may comprise any polypeptide and/or any other polymer (e.g., a synthetic or semi-synthetic polymer described herein).

In some of any of the embodiments described herein, the additional polymeric substance is covalently bound to the cross-linked polymer. In some embodiments, the additional polymeric substance is covalently linked to the cross-linked polymer via at least one cross-linking moiety such as described herein. In exemplary embodiments, the additional polymeric substance is covalently linked to the cross-linked polymer via at least one amide bond.

In some of any of the embodiments described herein, the additional polymeric substance is covalently bound to a resilin polypeptide moiety of the cross-linked polymer. In some embodiments, the resilin polypeptide moiety is linked to the polymeric substance by a cross-linking moiety described herein.

In some of any of the embodiments described herein, an additional polymeric substance covalently bound to the cross-linked polymer comprises a polypeptide. In exemplary embodiments, the polypeptide comprises collagen.

In some of any of the embodiments described herein, the additional polymeric substance is non-covalently bound to the cross-linked polymer.

In some of any of the embodiments described herein, the binding of the cross-linked polymer to the additional polymeric substance is effected by binding of a polysaccharide to a polysaccharide-binding domain (e.g., a polysaccharide-binding domain as described herein), for example, a cellulose binding domain and/or a chitin-binding domain. In exemplary embodiments, the polysaccharide is cellulose, which is bound by a cellulose-binding domain.

In some of any of the embodiments described herein, a composition-of-matter comprises a polysaccharide (e.g., as part of a polymeric moiety), and the additional polymeric substance (e.g., a polypeptide) of the composite material comprises a polysaccharide-binding domain which binds to the polysaccharide.

In some of any of the embodiments described herein, a composition-of-matter comprises a polysaccharide-binding domain (e.g., as part of a polypeptide), and the additional polymeric substance of the composite material comprises a polysaccharide which binds to the polysaccharide-binding domain. In some embodiments, the polysaccharide-binding domain is comprised by a polymeric moiety as described herein. In exemplary embodiments, the polysaccharide-binding domain is comprised by a resilin polypeptide moiety as described herein. Examples of resilin polypeptide sequences comprising a polysaccharide-binding domain are presented herein.

In some of any of the embodiments described herein, the composition-of-matter and/or composite material described herein is in a form of foam.

In some of any of the embodiments described herein, the composite material comprises the composition-of-matter (as described herein) in a form of a foam, further comprising an additional polymeric substance (as described herein) bound to at least a portion of the composition-of-matter.

In some of any of the embodiments described herein, the composite material comprises the additional polymeric substance (as described herein) in a form of a foam, further comprising the composition-of-matter (as described herein) bound to at least a portion of the additional polymeric substance.

In some of any of the embodiments described herein, the composition-of-matter, without an additional polymeric substance described herein, is in a form of a foam.

In some of any of the embodiments described herein, a porosity of the foam is at least 50%. In some embodiments, the porosity is at least 60%. In some embodiments, the porosity is at least 70%. In some embodiments, the porosity is at least 80%. In some embodiments, the porosity is at least 90%. In some embodiments, the porosity is at least 95%. In some embodiments, the porosity is at least 98%. In some embodiments, the porosity is at least 99%.

In some e of any of the embodiments described herein, the foam is elastic upon compression.

In some of any of the embodiments described herein, the foam is characterized by an elastic modulus (Young's modulus) of at least 2.5 kPa, upon compression. In some embodiments, the elastic modulus is at least 10 kPa. In some embodiments, the elastic modulus is at least 15 kPa. In some embodiments, the elastic modulus is at least 20 kPa. In some embodiments, the elastic modulus is at least 25 kPa. In some embodiments, the elastic modulus is at least 30 kPa. In some embodiments, the elastic modulus is at least 40 kPa. In some embodiments, the elastic modulus is at least 50 kPa. Any value higher than the above-indicated values is contemplated.

In exemplary embodiments, an elastic modulus of a foam formed from a composition-of-matter as described herein, which is not a part of a composite material as described herein, is in a range of from about 2.5 kDa to about 10 kDa.

In further exemplary embodiments, an elastic modulus of a foam formed from a composite material as described herein, is in a range of from about 15 kDa to about 80 kDa. Any value between the above-indicated values is contemplated.

As described herein, and exemplified in the Examples herein, the elastic modulus and elasticity of a foam can be modulated depending on whether it comprises a composite material as described herein, and by the process for preparing the foam.

Herein, properties measured under compression refer to compression at a rate of 2 mm per minute, following contact with an aqueous medium, as described herein.

In some of any of the embodiments described herein, the elasticity is characterized in that the elastic modulus decreases by no more than 50% following one cycle of compression by 40% (i.e., compression which reduces a height of a material along the axis of compression by 40%). In some embodiments, the elastic modulus decreases by no more than 40% following one cycle of compression by 40%. In some embodiments, the elastic modulus decreases by no more than 30% following one cycle of compression by 40%. In some embodiments, the elastic modulus decreases by no more than 20% following one cycle of compression by 40%. In some embodiments, the elastic modulus decreases by no more than 10% following one cycle of compression by 40%.

In some of any of the embodiments described herein, the foam is characterized by a resilience, upon compression, of at least 50%. In some embodiments, the resilience is at least 60%. In some embodiments, the resilience is at least 70%. In some embodiments, the resilience is at least 80%. In some embodiments, the resilience is at least 90%. In some embodiments, the resilience is at least 95%. In some embodiments, the resilience is at least 98%. In some embodiments, the resilience is at least 99%. In some embodiments, the resilience is at least 99.5%. In some embodiments, the foam is characterized by both a resilience as described herein and by an elastic modulus as described herein.

Herein and in the art, "resilience" is defined as the ratio of energy given up in recovery from deformation to the energy required to produce the deformation. Hysteresis is the percent energy loss per cycle of deformation, and is the result of internal friction.

Resilience can be measured using two routine methods, in accordance to the sample properties, geometry and preparation. For macroscopic samples such as foams, gels, etc., resilience can be measured on a tensile/compression tester (e.g., an Instron tester). For samples such as thin films and thin structures, it is accepted in the art to use scanning probe microscopy (SPM) to measure the stiffness and resilience of materials with spatial resolution of nanometers, as described for example, by Huson & Maxwell [*Polymer Testing* 2006, 25:2-11].

By measuring the area under the approach and retract curves of a force-distance plot, the resilience can be expressed as:

$$\text{Resilience} = 100(P-R)/(P+Q-R)$$

wherein:

P is the area under the force-distance retract curve;

Q is the area between the force-distance approach and retract curves (hysteresis); and R is the area under the force-distance approach curve when there is no penetration, i.e., on a hard surface.

In some of any of the embodiments described herein, the composite material comprises the cross-linked polymer of the composition-of-matter embedded in the additional polymeric substance(s). Such a polymeric substance is also referred to herein as a "matrix". In some embodiments, the cross-linked polymer is in a form of particles (e.g., as described herein) embedded in the matrix.

In some of any of the embodiments described herein, the embedded cross-linked polymer is not covalently bound to the polymeric substance(s) of the matrix. For example, the c\bond between the cross-linked polymer and polymeric substance(s) of the matrix may consist essentially of physical entrapment of the cross-linked polymer in the matrix.

In some of any of the embodiments described herein, the embedded cross-linked polymer is covalently bound to the polymeric substance(s) (e.g., as described herein).

According to another aspect of embodiments of the invention, there is provided an article-of-manufacturing comprising a composition-of-matter as described herein and/or a composite material as described herein.

According to some of any of the embodiments described herein, the composition-of-matter and/or a composite material is used for increasing the elasticity of at least a portion of the article-of-manufacturing.

Compositions-of-matter and/or a composite materials according to many embodiments described herein are highly biocompatible, due in part to the biocompatibility of resilin polypeptides.

Hence, in some of any of the embodiments described herein, the article-of-manufacturing is a medical device. In some embodiments, the composition-of-matter and/or a composite material is fashioned into a device or a component thereof. In some embodiments, the device consists essentially of the composition-of-matter and/or a composite material.

In some of any of the embodiments described herein, the medical device is an implantable medical device.

In some of any of the embodiments described herein, the article-of-manufacturing as described herein is for treating a tissue damage or loss (e.g., an implantable medical device for being implanted in a subject).

In another aspect of embodiments of the invention, there is provided a use of an article-of-manufacturing as described herein in the manufacture of a medicament for treating a tissue damage or loss (e.g., an implantable medical device for being implanted in a subject).

In another aspect of embodiments of the invention, there is provided a method of treating a tissue damage or loss, the method comprising implanting an article-of-manufacturing as described herein (e.g., an implantable medical device as described herein) in a subject.

In some embodiments of any of the aspects of described herein, the medical device is capable of forming a scaffold within a subject, to thereby induce formation of a tissue. The scaffold may be seeded with cells or not.

In some embodiments of any of the aspects of described herein, an implantable device may be, for example, a tissue, an organ or a synthetic implant such as a collagen based implant (e.g., wherein the polymeric moiety and/or additional polymeric substance comprises collagen), a mechanical device or a scaffold (e.g., a sponge). The implant may be temporary (e.g., biodegradable) or permanent.

The biodegradability may be modulated by selecting suitable properties of the polymeric moiety and/or additional polymeric substance described herein, and/or a degree of cross-linking. In general, cross-linking reduces biodegradability, and biodegradability of polymers in the polymeric moiety and/or additional polymeric substance described herein enhances biodegradability of the composition-of-matter and/or a composite material.

According to some embodiments, a medical device is used to strengthen a tissue, for example, by preventing kinking of a tissue, and or inhibiting leakage of a bodily fluid (e.g., blood) from a vessel (e.g., a blood vessel).

In some of any of the embodiments described herein, the device is used to treat an aneurysm, for example, by strengthening a vessel wall.

In order to strengthen a tissue, in some embodiments an implantable device (e.g., comprising a composition-of-matter and/or a composite material in a form of a membrane) is placed over a surface (e.g., an external surface) of the relevant tissue (e.g., over an aneurysm), and attached to the tissue, thereby allowing the implant to strengthen to strengthen the tissue.

It is to be appreciated that the considerable elasticity of compositions-of-matter and composite materials according to some embodiments of the invention renders them particularly suitable for strengthening moving materials, such as many types of tissue (e.g., blood vessel walls, ligaments, tendons, tissues in joints).

According to some embodiments, the implantable device is for bone and/or joint replacement. In some embodiments, the device is implanted at a ligament, tendon, cartilage, intervertebral disc or bone tissue.

Thus for example, in some of any of the embodiments described herein, the device is placed at a desired location in bone in such conditions such as non-union fractures, osteoporosis, of periodontal disease or defect, osteolytic bone disease, post-plastic surgery, post-orthopedic implantation, post neurosurgical surgery that involves calvaria bone removal, in alveolar bone augmentation procedures, for spine fusion and in vertebral fractures.

In some of any of the embodiments described herein wherein administration of the implant is for generation of tendon/ligament tissue, the implant is placed at a desired location in tendon/ligament following tissue tear due to trauma or inflammatory conditions.

In some of any of the embodiments described herein wherein administration of the implant is for generation of cartilage tissue, the implant is placed at a desired location in cartilage to treat defects due to conditions such as, but not limited to, rheumatoid arthritis, osteoarthritis, trauma, cancer surgery and cosmetic surgery.

In some of any of the embodiments described herein wherein administration of the implant is for generation of intervertebral disc tissues, including nucleus pulposus and annulus fibrosus, a device comprising a scaffold is placed at a desired location of nucleus pulposus degeneration, annulus fibrosus tears, or following nucleotomy or discectomy.

In some of any of the embodiments described herein, the composition-of-matter and/or composite material is configured for maintaining placement of an article-of-manufacturing in a cavity (e.g., by inhibiting slippage of the article-of-manufacturing), for example, maintaining placement of an implantable device in a body cavity. In some embodiments, such a role is facilitated by an elasticity of at least a portion of the article-of-manufacturing (e.g., an external portion). For example, placement in a cavity may comprise compression of at least a portion of the article-of-manufacturing, the compressive force applied to the article-of-manufacturing by the walls of the cavity aid in maintaining the placement of the article-of-manufacturing.

Examples of implantable devices whose placement may be maintained in a cavity include, without limitation, cardiovascular implants such as, for example, pacemakers, pacemaker casings, pacemaker leads, defibrillators, replacement heart valves, venous valves; angioplasty plugs, aortic aneurysm grafts, atrioventricular shunts, indwelling arterial catheters, indwelling venous catheters, synthetic vascular grafts, vascular aneurysm occluders, vascular prosthetic filters, vascular sheaths, patent foramen ovale septal closure devices and intra-vascular stents; catheters such as a hemodialysis catheter; hemodialysis grafts; stents and stent grafts such as tracheal stents, esophageal stents, urethral stents, and rectal stents; dental implants; orthopedic implants; bone fracture healing devices; bone replacement devices; joint replacement devices; guided tissue matrices; tissue regeneration devices; tumor targeting and destruction devices; suture anchors; drug delivery ports; hernia repair devices; and periodontal devices.

The device may be in a shape, for example, of a screw, a pin, a tack, a rod, a mesh (e.g., a suture mesh), a fiber, a fabric, a film, a spring, a coil, a clip, a ring, a needle, a sleeve, a tube, a strip, a sheet, a patch, and/or a plate.

In some of any of the embodiments described herein, the article-of-manufacturing is used in a non-medical application, for example, used as a flexible material. Examples of applications include, but are not limited to roofing sheets, swimming pool liners, reservoir liners, hoses, bathroom devices, industrial piping, rainwear, boots, covering materials such as food and drink coverings and/or containers.

According to another aspect of embodiments of the invention, there is provided a process for preparing a composition-of-matter as described herein. The process comprises covalently cross-linking a resilin polypeptide (e.g., as described herein) to at least one polymeric substance (e.g., a polymer described herein). In some embodiments, the resilin polypeptide and/or polymeric substance are essentially the same as a resilin polypeptide moiety and/or polymeric moiety as described herein, in the absence of cross-linking. In some embodiments, the cross-linking is selected such that it does not produce a biphenyl moiety, as described herein.

In some of any of the embodiments described herein, the polymeric substance(s) comprises a plurality of amine groups (e.g., as described herein). In some embodiments, cross-linking comprises reacting amine groups with a carboxylic group of the resilin polypeptide, to thereby form an amide bond (e.g., as described herein).

In some of any of the embodiments described herein, the process comprises activating a carboxylic group (e.g., a carboxylic group of a resilin polypeptide), and contacting a substance comprising the activated carboxylic group (e.g., a resilin polypeptide as described herein) with a substance comprising an amine group (e.g., a polymeric substance as described herein), to thereby form an amide bond (e.g., as described herein).

In some of any of the embodiments described herein, activation of a carboxylic group is effected by reaction with a carbodiimide. Various suitable carbodiimide reagents are known in the art. In exemplary embodiments, the carbodiimide comprises EDC (1-ethyl-3-[3-dimethylaminopropyl] carbodiimide).

In exemplary embodiments, reaction with a carbodiimide further comprises reaction with NHS (N-hydroxysuccinimide) or a substituted derivative thereof.

In some of any of the embodiments described herein, the process comprises contacting a hydrophilic solution (e.g., an aqueous solution) comprising the resilin polypeptide and at least one polymeric substance(s) with a hydrophilic surface prior to cross-linking. By cross-linking a solution on a hydrophilic surface, a composition-of-matter in a form of a membrane (e.g., as described herein) may be formed. Examples of hydrophilic surfaces include metals, glasses and hydrophilic polymers. In exemplary embodiments, a glass surface is treated with an acid, such as concentrated sulfuric acid, in order to enhance the hydrophilicity thereof.

In some of any of the embodiments described herein, a thickness of the membrane is controlled by controlling the hydrophilicity of the surface. In general, the more hydrophilic a surface, the more a hydrophilic solution will spread on the surface, resulting in a thinner membrane upon cross-linking.

In some of any of the embodiments described herein, the resilin polypeptide is in a form of a foam (a "resilin foam"). In exemplary embodiments, the resilin foam is contacted with the at least one polymeric substance (e.g., immersed in a liquid comprising the polymeric substance(s)) prior to cross-linking, to thereby contact the resilin polypeptide and the at least one polymeric substance with the polymeric substance(s).

In some of any of the embodiments described herein, the process further comprises preparing a plurality of particles comprising the resilin polypeptide and the polymeric substance(s), as described herein, prior to cross-linking.

Various techniques known in the art may be used for preparing particles from a mixture of resilin polypeptide and polymeric substance(s), including, without limitation, dispersion; ultrasound agitation; addition of an anti-solvent (e.g., carbon dioxide) to a solution (e.g., an aqueous solution); solvent extraction and/or evaporation; and/or sedimentation. Examples of such techniques are described in the Examples section herein.

In some of any of the embodiments described herein, the particles are formed from the dispersed phase of a dispersion (e.g., an emulsion). In some embodiments, the particles comprise an aqueous solution. In some embodiments, the aqueous solution is emulsified as a water-in-oil emulsion.

Herein and in the art, the term "dispersion" refers to a system in which particles of a substance are dispersed in a continuous phase of a different substance or state of the substance. Dispersions include, for example, systems comprising liquid and/or solid particles dispersed in a gas (which are referred to as aerosols), systems comprising gas particles dispersed in a liquid and/or solid (which are referred to as foams) systems comprising liquid particles dispersed in a liquid (which are referred to as emulsions), systems comprising solid particles dispersed in a liquid (which are referred to as sols or suspensions), and systems comprising liquid particles dispersed in a solid (which are referred to as gels or sponges (with absorbed liquid), depending on their consistency).

In some of any of the embodiments described herein, cross-linking of the resilin polypeptide and polymeric substance(s) within a particle causes substantially liquid and/or semisolid particles to solidify, to thereby form solid particles.

In some of any of the embodiments described herein, the particles are cross-linked to one another. In some embodiments, cross-linking of particles to one another is performed by substantially the same process as cross-linking of the resilin polypeptide with the polymeric substance(s) (e.g., as described herein).

In some of any of the embodiments described herein, the resilin polypeptide and polymeric substance(s) are cross-linked (e.g., as described herein) to form particles comprising a cross-linked polymer as described herein, and the particles are then cross-linked to one another. The cross-linking of the particles may be performed by any cross-linking process known in the art, and may be a process different than or substantially the same as the process of cross-linking the resilin polypeptide with the polymeric substance(s).

In some of any of the embodiments described herein, the cross-linking of the resilin polypeptide with the polymeric substance(s) within a particle and the cross-linking of the particles to one are performed concomitantly. In some embodiments, cross-linking of particles to one another is performed by substantially the same process as cross-linking of the resilin polypeptide with the polymeric substance(s) (e.g., as described herein).

In some of any of the embodiments described herein, the process is for preparing a composite material as described herein.

In some of any of the embodiments described herein, the process comprises contacting the resilin polypeptide and the at least one polymeric substance with at least one additional polymeric substance (e.g., as described herein) prior to cross-linking of the resilin polypeptide and the at least one polymeric substance. In some embodiments, the cross-linking covalently cross-links an additional polymeric substance with the resilin polypeptide and/or polymeric substance. In some embodiments, the cross-linking does not covalently cross-link the additional polymeric substance (a) with the resilin polypeptide and/or polymeric substance.

In some of any of the embodiments described herein, the at least one additional polymeric substance is mixed with the resilin polypeptide prior to cross-linking. In some embodiments, the at least one additional polymeric substance is mixed with the resilin polypeptide prior to contact with the polymeric substance(s) that is cross-linked with the resilin polypeptide.

In some of any of the embodiments described herein, the at least one additional polymeric substance is in a form of a foam. Such foams may be used to form a composite material in a form of a foam, as described herein. In some embodiments, the foam further comprises the resilin polypeptide. In some embodiments, the foam does not comprise the resilin polypeptide.

In some exemplary embodiments, the foam is contacted with the resilin polypeptide and the at least one polymeric substance (e.g., immersed in a liquid comprising the resilin polypeptide and polymeric substance(s)) prior to cross-linking, to thereby contact the resilin polypeptide and the at least one polymeric substance with the additional polymeric substance(s).

In some exemplary embodiments, the foam is formed from a mixture of the additional polymeric substance(s) and resilin polypeptide, and is then contacted, prior to cross-linking, with the polymeric substance(s) that is cross-linked with resilin polypeptide (e.g., immersed in a liquid comprising the polymeric substance(s)), to thereby contact the resilin polypeptide and the at least one polymeric substance with the additional polymeric substance(s).

In some of any of the embodiments described herein, a foam is formed by lyophilization of a suspension comprising a substance from which the form is formed. In some embodiments, the suspension is an aqueous suspension. Lyophilization may be used to prepare any type of foam described herein, including foams formed from a composition-of-matter described herein, a composite material described herein, a resilin polypeptide described herein, and/or an additional polymeric substance described herein.

In some of any of the embodiments described herein, the process further comprises embedding particles comprising the composition-of-matter (prepared as described herein) in at least one additional polymeric substance (as described herein), to thereby form a composite material comprising embedded particles, as described herein.

In some of any of the embodiments described herein, the particles are covalently cross-linked to one another (e.g., as described herein) prior to embedding.

In some of any of the embodiments described herein, the particles are not cross-linked to one another prior to embedding, and are covalently cross-linked to one another (e.g., as described herein) concomitantly with and/or subsequent to embedding.

In some of any of the embodiments described herein, the particles are not covalently cross-linked to one another, either before, during or after embedding.

In some of any of the embodiments described herein, cross-linking of particles to one another is performed by substantially the same process as cross-linking of the resilin polypeptide with the polymeric substance(s) (e.g., as described herein).

In some of any of the embodiments described herein, the composition-of-matter (e.g., in a form of particles) is covalently cross-linked with the additional polymeric substance(s). Such cross-linking may be performed by any cross-linking process known in the art, and may be a process different than or substantially the same as the process of cross-linking the resilin polypeptide with the polymeric substance(s) (e.g., as described herein).

In some of any of the embodiments described herein, the cross-linking of the resilin polypeptide with the polymeric substance(s) within a particle and the cross-linking of the particles of composition-of-matter to the additional polymeric substance(s) are performed concomitantly. In some embodiments, cross-linking of particles to the additional polymeric substance(s) is performed by substantially the same process as cross-linking of the resilin polypeptide with the polymeric substance(s) (e.g., as described herein).

As used herein, the term "amine" describes a —NRxRy group, wherein Rx and Ry are each independently hydrogen, alkyl, cycloalkyl, heteroalicyclic, heteroaryl or aryl, as these terms are defined herein. When Rx or Ry is heteroalicyclic or heteroaryl, the neighboring (nitrogen) atoms are bound to a carbon atom in the heteroalicyclic or heteroaryl.

The term "alkyl", as used herein, describes a saturated aliphatic hydrocarbon including straight chain and branched chain groups. Preferably, the alkyl group has 1 to 20 carbon atoms. Whenever a numerical range; e.g. "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. Substituted alkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine.

The alkyl group can be an end group, as this phrase is defined herein, wherein it is attached to a single adjacent atom, or a linking group e.g. an alkylene, as this phrase is defined herein, which connects two or more moieties.

Herein throughout, the phrase "end group" describes a group (a substituent) that is attached to a single moiety in the compound via one atom thereof.

The phrase "linking group" describes a group (a substituent) that is attached to two or more moieties in the compound.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine. The aryl group can be an end group, as this term is defined hereinabove, wherein it is attached to a single adjacent atom, or a linking group, as this term is defined hereinabove, connecting two or more moieties.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, carboxy, thiocarbamate, urea, thiourea, carbamate, amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties. Representative examples are piperidine, piperazine, tetrahydrofuran, tetrahydropyran, morpholine and the like.

The term "phosphonate" refers to an —O—P(=O)(ORx)- end group or a —O—P(=O)—O—, with Rx as defined hereinabove.

The term "halide" and "halo" describes fluorine, chlorine, bromine or iodine.

The term "sulfoxide" or "sulfinyl" describes a —S(=O)Rx end group or an —S(=O)— linking group, as these phrases are defined hereinabove, where Rx is as defined hereinabove.

The terms "sulfonate" and "sulfonyl" describe a —S(=O)$_2$—Rx end group or an —S(=O)$_2$— linking group, as these phrases are defined hereinabove, where Rx is as defined herein.

The term "sulfonamide", as used herein, encompasses both S-sulfonamides and N-sulfonamides.

The term "S-sulfonamide" describes a —S(=O)$_2$—NRxRy end group or a —S(=O)$_2$—NRx- linking group, as these phrases are defined hereinabove, with Rx and Ry as defined herein.

The term "N-sulfonamide" describes an RxS(=O)$_2$—NR$_y$— end group or a —S(=O)$_2$—NRx- linking group, as these phrases are defined hereinabove, where Rx and Ry are as defined herein.

The term "carbonyl" as used herein, describes a —C(=O)—Rx end group or a —C(=O)— linking group, as these phrases are defined hereinabove, with Rx as defined herein.

The terms "hydroxy" and "hydroxyl" describe a —OH group.

The term "oxo" describes a =O group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The terms "cyano" and "nitrile" describe a —C≡N group.

The term "nitro" describes an —NO$_2$ group.

The term "azo" describes an —N=NR' end group or an —N=N— linking group, as these phrases are defined hereinabove, with R' as defined hereinabove.

The terms "carboxy" and "carboxyl", as used herein, encompasses both C-carboxy and O-carboxy groups.

The term "C-carboxy" describes a —C(=O)—ORx end group or a —C(=O)—O— linking group, as these phrases are defined hereinabove, where Rx is as defined herein.

The term "O-carboxy" describes a —OC(=O)—Rx end group or a —OC(=O)— linking group, as these phrases are defined hereinabove, where R' is as defined herein.

The term "urea" describes a —NRxC(=O)—NRyRw end group or a —NR$_x$C(=O)—NR$_y$— linking group, as these phrases are defined hereinabove, where Rx and Ry are as defined herein and Rw is as defined herein for Rx and Ry.

The term "thiourea" describes a —NRx-C(=S)—NRyRw end group or a —NRx-C(=S)—NRy- linking group, with Rx, Ry and Ry as defined herein.

The term "amide", as used herein, encompasses both C-amides and N-amides.

The term "C-amide" describes a —C(=O)—NRxRy end group or a —C(=O)—NRx-linking group, as these phrases are defined hereinabove, where Rx and Ry are as defined herein.

The term "N-amide" describes a RxC(=O)—NRy- end group or a RxC(=O)—N-linking group, as these phrases are defined hereinabove, where Rx and Ry are as defined herein.

The term "carbamyl" or "carbamate", as used herein, encompasses both N-carbamates and O-carbamates.

The term "N-carbamate" describes an RyOC(=O)—NRx- end group or a —OC(=O)—NRx- linking group, as these phrases are defined hereinabove, with Rx and Ry as defined herein.

The term "O-carbamate" describes an —OC(=O)—NRxRy end group or an —OC(=O)—NRx- linking group, as these phrases are defined hereinabove, with Rx and Ry as defined herein.

The term "thiocarbamyl" or "thiocarbamate", as used herein, encompasses both O-thiocarbamates and N-thiocarbamates.

The term "O-thiocarbamate" describes a —OC(=S)—NRxRy end group or a —OC(=S)—NRx- linking group, as these phrases are defined hereinabove, with Rx and Ry as defined herein.

The term "N-thiocarbamate" describes an RyOC(=S)NRx- end group or a —OC(=S)NRx- linking group, as these phrases are defined hereinabove, with Rx and Ry as defined herein.

The term "guanyl" describes a RxRyNC(=N)— end group or a —RxNC(=N)— linking group, as these phrases are defined hereinabove, where Rx and R$_y$ are as defined herein.

The term "guanidine" describes a —RxNC(=N)—NRyRw end group or a —RxNC(=N)—NRy- linking group, as these phrases are defined hereinabove, where Rx, Ry and Rw are as defined herein.

The term "hydrazine", as used herein, describes a —NRx-NRyRw end group or a —NR$_x$—NRy- linking group, as these phrases are defined hereinabove, with Rx, Ry, and Rw as defined herein.

As used herein the term "about" refers to ±10%.

The terms "comprises", "comprising", "includes", "including", "having" and their conjugates mean "including but not limited to".

The term "consisting of" means "including and limited to".

The term "consist essentially of" and its conjugates means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions illustrate some embodiments of the invention in a non-limiting fashion.

Materials and Methods

Materials:

8-Arm amine terminated poly(ethylene glycol) (PEG-amine; 10,000 Da) was obtained from JenKem Technology U.S.A. (Allen, Tex.).

Collagen (Collage™ human recombinant collagen) was obtained from CollPlant (Israel).

Isopropanol and Span 80 were obtained from Merck.

EDC (1-ethyl-3-[3-dimethylaminopropyl]carbodiimide), NHS (N-hydroxysuccinimide), and ethanol were obtained from Sigma Aldrich.

Microcrystalline cellulose was obtained from Avicel.

Resilin Production:

Recombinant resilin was produced as a histidine-tagged (6H) chimeric protein composed of *D. melanogaster* resilin exon 1 (17 repeats) fused to *C. cellulovorans* cellulose binding domain (CBD). This recombinant resilin was produced in *E. coli*, extracted and purified as described in Qin et al. [*Biomacromolecules* 2009, 10:3227-3234], International Patent Application No. PCT/IL2008/001542 (published as WO 2009/069123) and Qin et al. [*Biomaterials* 2011, 32:9231-9243], resulting in a protein yield of about 100 mg/l.

The protein was analyzed by Western blot, and affinity to cellulose was confirmed by a cellulose binding assay performed similarly to the chitin binding assay described in Qin et al. [*Biomacromolecules* 2009, 10:3227-3234]. The cellulose binding was specific, occurring in resilin with a CBD but not in native resilin (lacking a CBD) used as a control.

In some experiments, the histidine-tagged protein was used. In other experiments, the histidine tag was cleaved prior to use of the protein using a recombinant histidine-tagged Tobacco Etch Virus (rTEV) protease as described by Kapust et al. [*Protein Eng* 2001, 14:993-1000], followed by repurification on a Ni-NTA column to remove the protease and cleaved histidine tag (the protein was collected from the flow through).

The gene and protein sequence for the resilin with CBD (and with the histidine tag, which may optionally be removed) are depicted in FIG. 1.

Nanocrystalline Cellulose Production:

Nanocrystalline cellulose (NCC) was prepared by controlled $H_2SO_4$ hydrolysis of 200 μm microcrystalline cellulose, as described by Bondeson et al. [*Cellulose* 2006, 13:171]. The NCC structure was observed by transmission electron microscopy, after a sample of 0.2% NCC was mounted on a thin carbon support and stained with uranyl acetate.

As shown in FIGS. 2A and 2B, a honey-like viscous crystal suspension was obtained (FIG. 2A) containing nanorods characterized by a width of about 10-20 nm and a length of about 200-400 nm (FIG. 2B).

Preparation and Characterization of Nanocrystalline Cellulose Foams:

Suspensions of 2.5% nanocrystalline cellulose (NCC) were cast in ELISA plate wells used as molds, and frozen at a temperature of −80° C., followed by lyophilization, resulting in cylindrical foams of approximately 6 mm in diameter and 7.6 mm in height. The NCC foams were then characterized upon being released from the molds by gluing the foam samples to metal supports, coated with gold, and observed by a JEM 5410 LV scanning electron microscope (Jeol, Japan).

As shown in FIGS. 3A and 3B, lyophilization resulted in a porous foam (FIG. 3A) which exhibited a nanostructure characterized by laminated sheets (FIG. 3B). The thickness of the sheets was approximately 10 nm, indicating that the sheet thickness represents the dimensions of a single NCC crystal.

These results suggest that cryo-concentration occurs upon freezing, causing local aggregation of NCC, which results in a porous network instead of the film that normally forms by NCC self-assembly [de Souza Lima & Borsali, *Macromol Rapid Comm* 2004, 25:771-787].

Mechanical Testing:

Mechanical tests of foams were performed using a MultiTest 1-i computerized tensile tester (Mecmesin, UK) with an ILC 10N load cell set on compression test mode, at a compression rate of 2 mm/minute. The bottom of the compression plate was flooded with phosphate buffer, which was also constantly pipetted on to the samples to ensure complete saturation. During compression, force (N) and displacement (mm) curves were recorded. Stress/strain curves were generated by dividing the force by the sample's surface area, and by dividing the displacement by the sample's height. The elastic modulus was represented by the slope of the linear regions of the curves.

Example 1

Preparation of Resilin and Resilin-Nanocrystalline Cellulose (NCC) Foams Cross-Linked with PEG-Amine Resilin-nanocrystalline cellulose (NCC) composite foams were prepared according to two different techniques. Resilin foams without NCC were also prepared.

The resilin contained a cellulose-binding domain (CBD) for effecting binding of resilin to NCC. Resilin was used after cleavage of the histidine tag, as described in the Materials and Methods section.

One type of resilin-NCC composite, referred to herein as "immersed composite", was prepared by immersing an NCC foam, which was prepared as described in the Materials and Methods section, in a solution of 200 mg/ml resilin in 20 mM sodium phosphate (pH 7.5). The resilin solution was added dropwise to the NCC foam, until the foam was fully saturated. The foam was then frozen at a temperature of −70° C. and lyophilized.

A second type of resilin-NCC composite, referred to herein as "mixed composite", was prepared by dissolving resilin in an NCC suspension prior to formation of a foam. 50 mg of lyophilized resilin powder was dissolved and mixed in 250 μl of a 2.5% NCC suspension, resulting in a resilin concentration of 200 mg/ml. The mixture was then frozen at a temperature of −70° C. and lyophilized. Eppendorf tube caps were used as molds, resulting in disks of approximately 5 mm in height and 5 mm in diameter.

In order to prepare a resilin foam, lyophilized recombinant resilin powder was suspended in 20 mM sodium phosphate (pH 7.5) at a concentration of 200 mg/ml. 200 μl samples of the solution were then cast into wells of an ELISA plate (diameter~6 mm) pre-treated with Sigmacote® siliconizing reagent to form a hydrophobic surface. The solutions were frozen at a temperature of −70° C. and lyophilized, resulting in formation of a resilin foam, with the wells serving as a mold.

All of the abovementioned types of foam were subjected to cross-linking of resilin in the foam.

In preliminary experiments, photo-induced polymerization was used to effect resilin cross-linking, using either Tris(bipyridine)ruthenium(II) chloride (according to procedures such as described in Elvin et al. [*Nature* 2005, 437:999-1002]) or a photo-induced Fenton system (as described in Qin et al., *Biomaterials* 2011, 32:9231-9243]). However, photo-induced polymerization did not consistently provide complete cross-linking in the inner portion of the foam, due to poor penetration of light, which resulted in an undesirable souffle-like structure (not shown).

Hence, an alternative method of cross-linking resilin, utilizing EDC (1-ethyl-3-(3-dimethylaminopropyl)carbodiimide hydrochloride), NHS (N-hydroxysuccinimide) and PEG-amine, was developed. It is to be appreciated that EDC does not significantly cross-link the resilin in the absence of the PEG-amine, because the resilin (and NCC) has little or no amine groups available for cross-linking. Prior to foam formation, NCC suspensions were titered with 1 M NaOH to a pH of 7, which is a suitable pH for the EDC/PEG-amine cross-linking.

The foams were incubated (in the dark) for 3 hours at room temperature in a solution of 50 mM EDC (1-ethyl-3-(3-dimethylaminopropyl)carbodiimide hydrochloride) and 6 mM NHS (N-hydroxysuccinimide) in a solvent of 90% isopropanol with 10% distilled deionized water (DDW). The following day, the foams were incubated in 0.1 M PBS with 100 mg/ml 8-arm PEG-amine for 1 hour at room temperature, and then washed twice with DDW. The foams were then incubated again (in the dark) for 3 hours at room temperature in a solution of 50 mM EDC and 6 mM NHS in 90% isopropanol with 10% DDW. The foams were then washed with DDW and allowed to dry at room temperature.

The mechanical properties of the resilin and resilin-NCC foams were assessed by compression testing. Pure NCC foams were tested for comparison. Prior to testing, the foams were saturated in DDW or 20 mM sodium phosphate (pH 7.5) for at least one hour, followed by 5 minutes of vacuum, to ensure full saturation.

As shown in FIG. 4, the elastic modulus of resilin-NCC composite foams were considerably higher than that of resilin foams. The elastic modulus of the resilin foams were 6.9±2.3 kPa, whereas the elastic modulus of resilin-NCC foams were 26.3±7.7 kPa for mixed composites, and 56.7±21.4 kPa for immersed composites.

The resilin and resilin-NCC foams were elastic and recovered their original shape after compression. In contrast, the NCC foam was plastic and did not recover its original shape. The elastic modulus of the NCC foam was 16±4.5 kPa.

These results indicate that the procedures described herein can produce an elastic cross-linked foam from resilin or a resilin-containing composite.

These results further indicate that the binding of resilin to a polymeric substance such as NCC resulted in additional strength.

Without being bound by any particular theory, it is believed that such an effect is analogous to the strengthening of naturally occurring resilin by association with chitin, which results in elastic modulus values as high as 2 MPa [Gosline et al., *Philos Trans R Soc Lond B Biol Sci* 2002, 357:121-132; Burrows et al., *BMC Biology* 2008, 6:41; Vincent & Wegst, *Arthropod Struct Dev* 2004, 33:187-199].

As shown in FIGS. 4 and 5A-5C, the elastic modulus and stress/strain curves of resilin foams and mixed composites did not change significantly over the course of 3 compression cycles, whereas the elastic modulus of immersed composites decreased from 56.7 kPa to about 27 kPa, a value similar to the elastic modulus of mixed composites.

These results indicate that the immersion of a preformed, highly ordered NCC network in resilin resulted in an especially strong structure in immersed composites, and that when this structure was compressed beyond a certain threshold, the network partially failed and the elastic modulus decreased, although the resilin-composite maintained the elasticity and strength of the relatively random network obtained in the mixed composites.

As shown in FIG. 6, resilin-NCC foam exhibited a greater resistance to stress under compression than did NCC foam. This result is in accordance with resilin-NCC foam having a higher elastic modulus than NCC foam, as shown in FIG. 4.

Without being bound by any particular theory, it is believed that the affinity of NCC to the cellulose-binding domain in the resilin resulted in additional strength of the resilin-NCC composites, even in the absence of a highly ordered network.

Example 2

Preparation of Resilin Membrane Cross-Linked with PEG-Amine

In view of the efficacy of the EDC/PEG-amine system for cross-linking resilin in foams, as exemplified in Example 1, EDC/PEG-amine cross-linking was performed in resilin-containing membranes. Recombinant resilin was prepared as described in the Materials and Methods section, without cleaving the histidine tags.

To form a resilin membrane, a glass surface was treated with concentrated sulfuric acid. This treatment result in a hydrophilic glass surface that was suitable for preparation of a hydrophilic resilin membrane.

Stock solutions of recombinant resilin (360 mg/ml) in 20 mM $Na_2HPO_4$ buffer (pH 8) and 8-arm PEG-amine (400 mg/ml) were mixed in a 3:1 ratio to a final concentration of 270 mg/ml resilin and 100 mg/ml PEG-amine. After solution homogenization, the resilin mixture was spread over the treated hydrophilic glass surface. The resulting membrane or fiber obtained from this spread solution was air dried overnight. Subsequently, the glass and the resilin fiber or membrane were immersed in a mixture composed of 80% isopropanol, 20% distilled deionized water (DDW), 50 mM EDC (1-ethyl-3-[3-dimethylaminopropyl]carbodiimide), and 25 mM NHS (N-hydroxysuccinimide) for 3 hours at room temperature in the dark in order to effect cross-linking. After cross-linking, the material was washed with DDW and removed from the glass.

An optical image of the produced cross-linked resilin-PEG material is presented in FIG. 7.

The mechanical properties of the membrane are optionally tested by compression tests such as described in the Materials and Methods section and/or by tensile testing of mechanical properties (e.g., tensile strength, elastic modulus and/or resilience) such as described by Elvin et al. [*Nature* 2005, 437:999-1002].

Example 3

Preparation of Resilin Cross-Linked with Collagen

EDC cross-linking was used to prepare resilin cross-linked with collagen. As collagen comprises amine groups available for cross-linking, PEG-amine was not included. Recombinant resilin was prepared as described in the Materials and Methods section, without cleaving the histidine tags.

A solution of recombinant resilin (3 mg/ml) in 20 mM $Na_2HPO_4$ buffer (pH 8) was mixed with a solution of fibrillated collagen in a 2:1 (resilin solution:collagen solution) ratio. Collagen fibrillation was induced by mixing a 3 mg/ml collagen stock solution (3 mg/ml in 10 mM HCl) with fibrillogenesis buffer (200 mM $Na_2HPO_4$, pH 11.2) in a 10:1 (collagen:fibrillogenesis buffer) ratio and incubating the mixture for 1 hour, at 37° C.

After solution homogenization, 50 mM EDC and 25 mM NHS were added to 55 ml of the mixed solution. The cross-linking reaction was subsequently conducted while stirring for 3 hours at room temperature. The cross-linked protein solution was then centrifuged (22° C., 9000 g, 10 minutes), and the obtained pellet was cast into a mold and air dried at room temperature overnight. The resilin-collagen membrane was then washed with DDW and removed from the mold.

An optical image of the produced cross-linked resilin-collagen membrane is presented in FIG. 8.

The mechanical properties of the membrane are optionally tested by compression tests such as described in the Materials and Methods section and/or by tensile testing of mechanical properties (e.g., tensile strength, elastic modulus and/or resilience) such as described by Elvin et al. [*Nature* 2005, 437:999-1002].

Example 4

Preparation of Resilin Spheres Cross-Linked with PEG-Amine

Small spheres of resilin cross-linked with PEG-amine were prepared using a modification of the EDC cross-linking procedures described in Example 2. The resilin spheres are useful for preparing composite materials. Recombinant resilin was prepared as described in the Materials and Methods section, without cleaving the histidine tags.

28 μl of 360 mg/ml resilin stock solution was mixed with 12.5 μl of a 400 mg/ml PEG-amine stock solution, and DDW was added to a final volume of 50 μl, thereby obtaining 200 mg/ml recombinant resilin mixed with 100 mg/ml PEG-amine in 20 mM $Na_2HPO_4$ (pH 8). This mixture was added dropwise, with stirring, to a 50 ml tube containing 2.5 ml castor oil and 1% Span 80 (a surfactant) in order to create a water-in-oil emulsion of non-cross-linked resilin spheres. An image of the non-cross-linked resilin spheres, obtained via optical microscope, is presented in FIG. 9.

Shortly thereafter, 50 mM EDC and 25 mM NHS in 2.5 ml of aqueous isopropanol (80% v/v) were added to the emulsion. The resulting mixture was stirred for 2.5 hours at room temperature in the dark, resulting in cross-linked spheres composed of resilin cross-linked with PEG-amine. The obtained mixture of cross-linked resilin spheres was then placed in ethanol while stirring for 5 minutes at room temperature. The cross-linked resilin spheres were then collected by centrifugation (23° C., 6000 g, 5 minutes).

An image of the cross-linked resilin spheres, obtained via optical microscope, is presented in FIG. 10.

The resilin spheres are optionally used to prepare a composite material by dispersing the spheres in a collagen gel, and then cross-linking the spheres to the collagen using EDC and NHS (e.g., using procedures such as described in Example 3) or glutaraldehyde. The obtained composite material is optionally lyophilized.

The mechanical properties of the composite material are optionally tested by compression tests such as described in the Materials and Methods section and/or by tensile testing of mechanical properties (e.g., tensile strength, elastic modulus and/or resilience) such as described by Elvin et al. [*Nature* 2005, 437:999-1002].

Example 5

Preparation of Cross-Linked Resilin Spheres by Alternative Methods

Preparation of Non-Cross-Linked Resilin Spheres Using Sedimentation:

Resilin spheres are prepared according to procedures described by Ruckenstein et al. [*Polymer* 1995, 36:2857-2860]. An aqueous monomer solution containing resilin is introduced dropwise with a syringe into a vertical glass column containing hot paraffin oil.

Preparation of Non-Cross-Linked Resilin Spheres Using Dispersion in Supercritical $CO_2$:

Resilin spheres are prepared according to procedures described by Benedetti et al. [*Biotechnol Bioeng* 1997, 53:232-237]. A solution containing resilin is expanded by using carbon dioxide as a supercritical antisolvent (SAS) in a batch mode.

Preparation of Non-Cross-Linked Resilin Spheres Using Solvent Extraction/Evaporation:

Resilin spheres are prepared according to procedures described by Freitas et al. [*Journal of Controlled Release* 2005, 102:313-332]. An emulsion (e.g., an oil-in water emulsion) is prepared with resilin dissolved or dispersed in the dispersed phase. The solvent of the dispersed phase is then removed via extraction and/or evaporation, resulting in resilin spheres.

Preparation of Non-Cross-Linked Resilin Spheres Using High Intensity Ultrasound:

Resilin spheres are prepared according to procedures described by Gedanken [*Chem Eur J* 2008, 14:3840-3853]. A solution (e.g., aqueous solution) comprising resilin (e.g., about 50 mg/ml resilin) is subjected to high intensity (e.g., from 20 kHz to 10 MHz) to ultrasound (e.g., for about 3 minutes), resulting in the formation of resilin micro-spheres, typically about 2.5 μm in diameter. Optionally, air-filled micro-spheres are prepared by directing the ultrasound to an air-water interface of the resilin solution. Optionally, organic liquid-filled micro-spheres are prepared by directing the ultrasound to an organic liquid-water interface of the resilin solution.

Resilin spheres prepared according to any of the above methods are cross-linked with EDC and PEG-amine and collected, using procedures described in Example 4. The cross-linked resilin spheres are optionally used to prepare a composite material, as described in Example 4.

The mechanical properties of the composite material are optionally tested by compression tests such as described in the Materials and Methods section and/or by tensile testing of mechanical properties (e.g., tensile strength, elastic modulus and/or resilience) such as described by Elvin et al. [*Nature* 2005, 437:999-1002].

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a cross-linked polymer, the cross-linked polymer comprising a plurality of resilin polypeptide moieties, and at least one polymeric moiety covalently cross-linked to a plurality of said resilin polypeptide moieties via at least one, wherein at least 10 weight percents of said cross-linked polymer is said at least one polymeric moiety and at least 10 weight percents of said cross-linked polymer is said resilin polypeptide moieties, and wherein said at least one polymeric moiety comprises a plurality of amine groups, and each of said at least one amide bond is formed from an amine group of said polymeric moiety and a carboxylic group of said resilin polypeptide moieties.

2. The composition-of-matter of claim 1, wherein at least 20 weight percents of said cross-linked polymer is said at least one polymeric moiety.

3. The composition-of-matter of claim 1, wherein said carboxylic group forms a part of a side chain of an amino acid residue of said resilin polypeptide selected from the group consisting of a glutamate residue and an aspartate residue.

4. The composition-of-matter of claim 1, wherein said at least one polymeric moiety comprises a branched amine-terminated polymer.

5. The composition-of-matter of claim 1, wherein said at least one polymeric moiety comprises a polypeptide.

6. The composition-of-matter of claim 5, wherein said polypeptide comprises a collagen.

7. The composition-of-matter of claim 5, wherein said amide bond is generated from a side chain of at least one lysine residue of said polymeric moiety.

8. The composition-of-matter of claim 1, wherein said at least one polymeric moiety comprises poly(ethylene glycol) (PEG).

9. The composition-of-matter of claim 1, wherein said cross-linked polymer is in a form of a plurality of particles.

10. The composition-of-matter of claim 9, wherein a diameter of said particles is in a range of from 1 μm to 200 μm.

11. The composition-of-matter of claim 9, wherein said particles are substantially spheroid.

12. The composition-of-matter of claim 9, wherein said particles are covalently cross-linked to one another.

13. The composition-of-matter of claim 1, being in a form of a membrane.

14. The composition-of-matter of claim 1, being in a form of a foam.

15. The composition-of-matter of claim 14, having at least one characteristic selected from the group consisting of:
   an elastic modulus of at least 2.5 kPa; and
   a resilience of at least 50%,
   upon compression of the foam.

* * * * *

```
                        SEQUENCE LISTING

<160> NUMBER OF SEQ ID NOS: 19

<210> SEQ ID NO 1
<211> LENGTH: 324
<212> TYPE: PRT
<213> ORGANISM: Artificial sequence
<220> FEATURE:
<223> OTHER INFORMATION: Drosophila melanogaster derived resilin exon 1

<400> SEQUENCE: 1

Met Gly Pro Glu Pro Pro Val Asn Ser Tyr Leu Pro Pro Ser Asp Ser
1               5                   10                  15

Tyr Gly Ala Pro Gly Gln Ser Gly Pro Gly Arg Pro Ser Asp Ser
            20                  25                  30

Tyr Gly Ala Pro Gly Gly Asn Gly Gly Arg Pro Ser Asp Ser Tyr
            35                  40                  45

Gly Ala Pro Gly Gln Gly Gln Gly Gln Gly Gln Gly Gln Gly Gly Tyr
        50                  55                  60

Ala Gly Lys Pro Ser Asp Thr Tyr Gly Ala Pro Gly Gly Gly Asn Gly
65                  70                  75                  80

Asn Gly Gly Arg Pro Ser Ser Ser Tyr Gly Ala Pro Gly Gly Gly Asn
                85                  90                  95

Gly Gly Arg Pro Ser Asp Thr Tyr Gly Ala Pro Gly Gly Gly Asn Gly
                100                 105                 110

Gly Arg Pro Ser Asp Thr Tyr Gly Ala Pro Gly Gly Gly Asn Gly
            115                 120                 125

Asn Gly Gly Arg Pro Ser Ser Ser Tyr Gly Ala Pro Gly Gln Gly Gln
    130                 135                 140

Gly Asn Gly Asn Gly Gly Arg Ser Ser Ser Tyr Gly Ala Pro Gly
145                 150                 155                 160

Gly Gly Asn Gly Gly Arg Pro Ser Asp Thr Tyr Gly Ala Pro Gly Gly
                165                 170                 175

Gly Asn Gly Gly Arg Pro Ser Asp Thr Tyr Gly Ala Pro Gly Gly Gly
            180                 185                 190

Asn Asn Gly Gly Arg Pro Ser Ser Ser Tyr Gly Ala Pro Gly Gly Gly
        195                 200                 205

Asn Gly Gly Arg Pro Ser Asp Thr Tyr Gly Ala Pro Gly Gly Gly Asn
    210                 215                 220

Gly Asn Gly Ser Gly Gly Arg Pro Ser Ser Tyr Gly Ala Pro Gly
225                 230                 235                 240

Gln Gly Gln Gly Gly Phe Gly Gly Arg Pro Ser Asp Ser Tyr Gly Ala
                245                 250                 255

Pro Gly Gln Asn Gln Lys Pro Ser Asp Ser Tyr Gly Ala Pro Gly Ser
            260                 265                 270

Gly Asn Gly Asn Gly Gly Arg Pro Ser Ser Tyr Gly Ala Pro Gly
        275                 280                 285

Ser Gly Pro Gly Gly Arg Pro Ser Asp Ser Tyr Gly Pro Pro Ala Ser
    290                 295                 300

Gly Ser Gly Ala Gly Gly Ala Gly Gly Ser Gly Pro Gly Gly Ala Asp
305                 310                 315                 320

Tyr Asp Asn Asp
```

```
<210> SEQ ID NO 2
<211> LENGTH: 323
<212> TYPE: PRT
<213> ORGANISM: Artificial sequence
<220> FEATURE:
<223> OTHER INFORMATION: Drosophila melanogaster derived resilin exon 1

<400> SEQUENCE: 2

Gly Pro Glu Pro Pro Val Asn Ser Tyr Leu Pro Pro Ser Asp Ser Tyr
1               5                   10                  15

Gly Ala Pro Gly Gln Ser Gly Pro Gly Gly Arg Pro Ser Asp Ser Tyr
            20                  25                  30

Gly Ala Pro Gly Gly Gly Asn Gly Gly Arg Pro Ser Asp Ser Tyr Gly
        35                  40                  45

Ala Pro Gly Gln Gly Gln Gly Gln Gly Gln Gly Gln Gly Gly Tyr Ala
    50                  55                  60

Gly Lys Pro Ser Asp Thr Tyr Gly Ala Pro Gly Gly Gly Asn Gly Asn
65                  70                  75                  80

Gly Gly Arg Pro Ser Ser Ser Tyr Gly Ala Pro Gly Gly Gly Asn Gly
                85                  90                  95

Gly Arg Pro Ser Asp Thr Tyr Gly Ala Pro Gly Gly Gly Asn Gly Gly
            100                 105                 110

Arg Pro Ser Asp Thr Tyr Gly Ala Pro Gly Gly Gly Asn Gly Asn
        115                 120                 125

Gly Gly Arg Pro Ser Ser Ser Tyr Gly Ala Pro Gly Gln Gly Gln Gly
    130                 135                 140

Asn Gly Asn Gly Gly Arg Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
                165                 170                 175

Asn Gly Gly Arg Pro Ser Asp Thr Tyr Gly Ala Pro Gly Gly Gly Asn
            180                 185                 190

Asn Gly Gly Arg Pro Ser Ser Ser Tyr Gly Ala Pro Gly Gly Gly Asn
        195                 200                 205

Gly Gly Arg Pro Ser Asp Thr Tyr Gly Ala Pro Gly Gly Gly Asn Gly
    210                 215                 220

Asn Gly Ser Gly Gly Arg Pro Ser Ser Ser Tyr Gly Ala Pro Gly Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Asn Gly Gly Arg Pro Ser Ser Ser Tyr Gly Ala Pro Gly Ser
        275                 280                 285

Gly Pro Gly Gly Arg Pro Ser Asp Ser Tyr Gly Pro Pro Ala Ser Gly
    290                 295                 300

Ser Gly Ala Gly Gly Ala Gly Gly Ser Gly Pro Gly Gly Ala Asp Tyr
305                 310                 315                 320

Asp Asn Asp

<210> SEQ ID NO 3
<211> LENGTH: 62
<212> TYPE: PRT
<213> ORGANISM: Artificial sequence
<220> FEATURE:
```

<223> OTHER INFORMATION: Chitin binding sequence

<400> SEQUENCE: 3

Glu Pro Ala Lys Tyr Glu Phe Asn Tyr Gln Val Glu Asp Ala Pro Ser
1               5                   10                  15

Gly Leu Ser Phe Gly His Ser Glu Met Arg Asp Gly Asp Phe Thr Thr
            20                  25                  30

Gly Gln Tyr Asn Val Leu Leu Pro Asp Gly Arg Lys Gln Ile Val Glu
        35                  40                  45

Tyr Glu Ala Asp Gln Gln Gly Tyr Arg Pro Gln Ile Arg Tyr
    50                  55                  60

<210> SEQ ID NO 4
<211> LENGTH: 15
<212> TYPE: PRT
<213> ORGANISM: Artificial sequence
<220> FEATURE:
<223> OTHER INFORMATION: Resilin repeating unit

<400> SEQUENCE: 4

Gly Gly Arg Pro Ser Asp Ser Tyr Gly Ala Pro Gly Gly Gly Asn
1               5                   10                  15

<210> SEQ ID NO 5
<211> LENGTH: 9
<212> TYPE: PRT
<213> ORGANISM: Artificial sequence
<220> FEATURE:
<223> OTHER INFORMATION: Resilin repeating unit

<400> SEQUENCE: 5

Gly Arg Pro Ser Asp Ser Tyr Gly Ala
1               5

<210> SEQ ID NO 6
<211> LENGTH: 74
<212> TYPE: PRT
<213> ORGANISM: Artificial sequence
<220> FEATURE:
<223> OTHER INFORMATION: Chitin binding sequence

<400> SEQUENCE: 6

Pro Ala Lys Tyr Glu Phe Asn Tyr Gln Val Glu Asp Ala Pro Ser Gly
1               5                   10                  15

Leu Ser Phe Gly His Ser Glu Met Arg Asp Gly Asp Phe Thr Thr Gly
            20                  25                  30

Gln Tyr Asn Val Leu Leu Pro Asp Gly Arg Lys Gln Ile Val Glu Tyr
        35                  40                  45

Glu Ala Asp Gln Gln Gly Tyr Arg Pro Gln Ile Arg Tyr Glu Gly Asp
    50                  55                  60

Ala Asn Asp Gly Ser Gly Pro Ser Gly Pro
65                  70

<210> SEQ ID NO 7
<211> LENGTH: 900
<212> TYPE: DNA
<213> ORGANISM: Artificial sequence
<220> FEATURE:
<223> OTHER INFORMATION: Examples of polynucleotides which can be used
      to express resilin

<400> SEQUENCE: 7
agctatggag caccgggtca gagtggtccc ggcggcaggc cgtcggattc ctatggagct      60

```
cctggtggtg gaaacggtgg acggccctca gacagctatg gcgctccagg ccagggtcaa      120
ggacagggac aaggacaagg tggatatgca ggcaagccct cagataccta tggagctcct      180
ggtggtggaa atggcaacgg aggtcgtcca tcgagcagct atggcgctcc tggcggtgga      240
aacggtggtc gtccttcgga tacctacggt gctcctggtg gcggaaatgg tggacgccca      300
tcggacactt atggtgctcc tggtggtggt ggaaatggca acggcggacg accttcaagc      360
agctatggag ctcctggtca aggacaaggc aacggaaatg gcggtcgctc atcgagcagc      420
tatggtgctc ctggcggtgg aaacggcggt cgtccttcgg atacctacgg tgctcccggt      480
ggtggaaacg gtggtcgtcc ttcggatact tacggcgctc ctggtggcgg caataatggc      540
ggtcgtccct caagcagcta cggcgctcct ggtggtggaa acggtggtcg tccatctgac      600
acctatggcg ctcctggtgg cggtaacgga aacggcagcg gtggtcgtcc ttcaagcagc      660
tatggagctc ctggtcaggg ccaaggtgga tttggtggtc gtccatcgga ctcctatggt      720
gctcctggtc agaaccaaaa accatcagat tcatatggcg cccctggtag cggcaatggc      780
aacggcggac gtccttcgag cagctatgga gctccaggct caggacctgg tggccgaccc      840
tccgactcct acggacccc cagcttctgga tcgggagcag gtggcgctgg aggcagtgga      900
```

<210> SEQ ID NO 8
<211> LENGTH: 1080
<212> TYPE: DNA
<213> ORGANISM: Artificial sequence
<220> FEATURE:
<223> OTHER INFORMATION: An exemplary DNA sequence of 6H-tagged resilin
      (exon 1)

<400> SEQUENCE: 8

```
atgtcgtact accatcacca tcaccatcac gattacgata tcccaacgac cgaaaacctg       60
tattttcagg gcgccatggg accggagcca ccagttaact cgtatctacc tccgtccgat      120
agctatggag caccgggtca gagtggtccc ggcggcaggc cgtcggattc ctatggagct      180
cctggtggtg gaaacggtgg acggccctca gacagctatg gcgctccagg ccagggtcaa      240
ggacagggac aaggacaagg tggatatgca ggcaagccct cagataccta tggagctcct      300
ggtggtggaa atggcaacgg aggtcgtcca tcgagcagct atggcgctcc tggcggtgga      360
aacggtggtc gtccttcgga tacctacggt gctcctggtg gcggaaatgg tggacgccca      420
tcggacactt atggtgctcc tggtggtggt ggaaatggca acggcggacg accttcaagc      480
agctatggag ctcctggtca aggacaaggc aacggaaatg gcggtcgctc atcgagcagc      540
tatggtgctc ctggcggtgg aaacggcggt cgtccttcgg atacctacgg tgctcccggt      600
ggtggaaacg gtggtcgtcc ttcggatact tacggcgctc ctggtggcgg caataatggc      660
ggtcgtccct caagcagcta cggcgctcct ggtggtggaa acggtggtcg tccatctgac      720
acctatggcg ctcctggtgg cggtaacgga aacggcagcg gtggtcgtcc ttcaagcagc      780
tatggagctc ctggtcaggg ccaaggtgga tttggtggtc gtccatcgga ctcctatggt      840
gctcctggtc agaaccaaaa accatcagat tcatatggcg cccctggtag cggcaatggc      900
aacggcggac gtccttcgag cagctatgga gctccaggct caggacctgg tggccgaccc      960
tccgactcct acggacccc cagcttctgga tcgggagcag gtggcgctgg aggcagtgga     1020
cccggcggcg ctgactacga taacgatgag ggatccaatc actagtgaat tcgcggccgc     1080
```

<210> SEQ ID NO 9
<211> LENGTH: 354

<212> TYPE: PRT
<213> ORGANISM: Artificial sequence
<220> FEATURE:
<223> OTHER INFORMATION: An exemplary [protein sequence of 6H-tagged resilin (exon 1)

<400> SEQUENCE: 9

Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
            35                  40                  45

Gly Pro Gly Gly Arg Pro Ser Asp Ser Tyr Gly Ala Pro Gly Gly Gly
        50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
                85                  90                  95

Tyr Gly Ala Pro Gly Gly Gly Asn Gly Asn Gly Gly Arg Pro Ser Ser
            100                 105                 110

Ser Tyr Gly Ala Pro Gly Gly Asn Gly Gly Arg Pro Ser Asp Thr
            115                 120                 125

Tyr Gly Ala Pro Gly Gly Gly Asn Gly Gly Arg Pro Ser Asp Thr Tyr
            130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Arg
            165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
            195                 200                 205

Asp Thr Tyr Gly Ala Pro Gly Gly Gly Asn Asn Gly Gly Arg Pro Ser
        210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
            245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
            275                 280                 285

Ser Asp Ser Tyr Gly Ala Pro Gly Ser Gly Asn Gly Asn Gly Gly Arg
        290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Ala
            325                 330                 335

Gly Gly Ser Gly Pro Gly Gly Ala Asp Tyr Asp Asn Asp Glu Gly Ser
            340                 345                 350

Asn His

<210> SEQ ID NO 10
<211> LENGTH: 1311

<212> TYPE: DNA
<213> ORGANISM: Artificial sequence
<220> FEATURE:
<223> OTHER INFORMATION: An exemplary DNA sequence of 6H-tagged resilin
      (exons 1 and 2)

<400> SEQUENCE: 10

```
catatgtcgt actaccatca ccatcaccat cacgattacg atatcccaac gaccgaaaac    60
ctgtattttc agggcgccat gggaccggag ccaccagtta actcgtatct acctccgtcc   120
gatagctatg gagcaccggg tcagagtggt cccggcggca ggccgtcgga ttcctatgga   180
gctcctggtg gtggaaacgg tggacggccc tcagacagct atggcgctcc aggccagggt   240
caaggacagg gacaaggaca aggtggatat gcaggcaagc cctcagatac ctatggagct   300
cctggtggtg gaaatggcaa cggaggtcgt ccatcgagca gctatggcgc tcctggcggt   360
ggaaacggtg gtcgtccttc ggataccta cggtgctcctg gtggcggaaa tggtggacgc   420
ccatcggaca cttatggtgc tcctggtggt ggtggaaatg gcaacggcgg acgaccttca   480
agcagctatg gagctcctgg tcaaggacaa ggcaacggaa atggcggtcg ctcatcgagc   540
agctatggtg ctcctggcgg tggaaacggc ggtcgtcctt cggataccta cggtgctccc   600
ggtggtggaa acggtggtcg tccttcggat acttacggcg ctcctggtgg cggcaataat   660
ggcggtcgtc cctcaagcag ctacggcgct cctggtggtg aaacggtgg tcgtccatct   720
gacacctatg gcgctcctgg tggcggtaac ggaaacggca gcggtggtcg tccttcaagc   780
agctatggag ctcctggtca gggccaaggt ggatttggtg gtcgtccatc ggactcctat   840
ggtgctcctg gtcagaacca aaaaccatca gattcatatg gcgcccctgg tagcggcaat   900
ggcaacggcg gacgtccttc gagcagctat ggagctccag gctcaggacc tggtggccga   960
ccctccgact cctacggacc cccagcttct ggatcgggag caggtggcgc tggaggcagt  1020
ggacccggcg gcgctgacta cgataacgat gagcccgcca agtacgaatt taattaccag  1080
gttgaggacg cgcccagcgg actctcgttc gggcattcag agatgcgcga cggtgacttc  1140
accaccggcc agtacaatgt cctgttgccc gacggaagga agcaaattgt ggagtatgaa  1200
gccgaccagc agggctaccg gccacagatc cgctacgaag gcgatgccaa cgatggcagt  1260
ggtcccagcg gtccttaagg atccgagctc cgtcgacaag cttgcggccg c            1311
```

<210> SEQ ID NO 11
<211> LENGTH: 424
<212> TYPE: PRT
<213> ORGANISM: Artificial sequence
<220> FEATURE:
<223> OTHER INFORMATION: An exemplary protein sequence of 6H-tagged
      resilin (exons 1 and 2)

<400> SEQUENCE: 11

```
Met Ser Tyr Tyr His His His His His His Asp Tyr Asp Ile Pro Thr
1               5                  10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
```

```
                     85                  90                  95
Tyr Gly Ala Pro Gly Gly Gly Asn Gly Asn Gly Gly Arg Pro Ser Ser
                100                 105                 110

Ser Tyr Gly Ala Pro Gly Gly Gly Asn Gly Gly Arg Pro Ser Asp Thr
            115                 120                 125

Tyr Gly Ala Pro Gly Gly Gly Asn Gly Gly Arg Pro Ser Asp Thr Tyr
        130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Arg
            165                 170                 175

Ser Ser Ser Tyr Gly Ala Pro Gly Gly Gly Asn Gly Gly Arg Pro
        180                 185                 190

Ser Asp Thr Tyr Gly Ala Pro Gly Gly Gly Asn Gly Gly Arg Pro Ser
            195                 200                 205

Asp Thr Tyr Gly Ala Pro Gly Gly Gly Asn Asn Gly Gly Arg Pro Ser
        210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
        275                 280                 285

Ser Asp Ser Tyr Gly Ala Pro Gly Ser Gly Asn Gly Asn Gly Gly Arg
    290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Pro Ala
        340                 345                 350

Lys Tyr Glu Phe Asn Tyr Gln Val Glu Asp Ala Pro Ser Gly Leu Ser
    355                 360                 365

Phe Gly His Ser Glu Met Arg Asp Gly Asp Phe Thr Thr Gly Gln Tyr
    370                 375                 380

Asn Val Leu Leu Pro Asp Gly Arg Lys Gln Ile Val Glu Tyr Glu Ala
385                 390                 395                 400

Asp Gln Gln Gly Tyr Arg Pro Gln Ile Arg Tyr Glu Gly Asp Ala Asn
            405                 410                 415

Asp Gly Ser Gly Pro Ser Gly Pro
            420

<210> SEQ ID NO 12
<211> LENGTH: 1580
<212> TYPE: DNA
<213> ORGANISM: Artificial sequence
<220> FEATURE:
<223> OTHER INFORMATION: An exemplary DNA sequence of 6H-tagged resilin
      (exon 1) fused to a cellulose-binding domain (CBD)

<400> SEQUENCE: 12
catatgtcgt actaccatca ccatcaccat cacgattacg atatcccaac gaccgaaaac     60
ctgtattttc agggcgccat gggaccggag ccaccagtta actcgtatct acctccgtcc    120
```

```
gatagctatg gagcaccggg tcagagtggt cccggcggca ggccgtcgga ttcctatgga      180
gctcctggtg gtggaaacgg tggacggccc tcagacagct atggcgctcc aggccagggt      240
caaggacagg gacaaggaca aggtggatat gcaggcaagc cctcagatac ctatggagct      300
cctggtggtg gaaatggcaa cggaggtcgt ccatcgagca gctatggcgc tcctggcggt      360
ggaaacggtg gtcgtccttc ggatacctac ggtgctcctg gtggcggaaa tggtggacgc      420
ccatcggaca cttatggtgc tcctggtggt ggtggaaatg caacggcgg acgaccttca      480
agcagctatg gagctcctgg tcaaggacaa ggcaacggaa atggcggtcg ctcatcgagc      540
agctatggtg ctcctggcgg tggaaacggc ggtcgtcctt cggataccta cggtgctccc      600
ggtggtggaa acggtggtcg tccttcggat acttacggcg ctcctggtgg cggcaataat      660
ggcggtcgtc cctcaagcag ctacggcgct cctggtggtg aaacggtgg tcgtccatct       720
gacacctatg gcgctcctgg tggcggtaac ggaaacggca gcggtggtcg tccttcaagc      780
agctatggag ctcctggtca gggccaaggt ggatttggtg tcgtccatc ggactcctat       840
ggtgctcctg gtcagaacca aaaaccatca gattcatatg gcgcccctgg tagcggcaat      900
ggcaacggcg gacgtcctcc gagcagctat ggagctccag gctcaggacc tggtggccga      960
ccctccgact cctacggacc ccagcttct ggatcgggag caggtggcgc tggaggcagt       1020
ggacccggcg gcgctgacta cgataacgat gaggggatcc ccgaccccgg catggcagcg      1080
acatcatcaa tgtcagttga attttacaac tctaacaaat cagcacaaac aaactcaatt      1140
acaccaataa tcaaaattac taacacatct gacagtgatt taaatttaaa tgacgtaaaa      1200
gttagatatt attacacaag tgatggtaca caaggacaaa ctttctggtg tgaccatgct      1260
ggtgcattat taggaaatag ctatgttgat aacactagca aagtgacagc aaacttcgtt      1320
aaagaaacag caagcccaac atcaacctat gatacatatg ttgaatttgg atttgcaagc      1380
ggacgagcta ctcttaaaaa aggacaattt ataactattc aaggaagaat aacaaaatca      1440
gactggtcaa actacactca aacaaatgac tattcatttg atgcaagtag ttcaacacca      1500
gttgtaaatc caaagttac aggatatata ggtggagcta agtacttgg tacagcacca      1560
taggatcgat ccagatgtac                                                  1580
```

<210> SEQ ID NO 13
<211> LENGTH: 519
<212> TYPE: PRT
<213> ORGANISM: Artificial sequence
<220> FEATURE:
<223> OTHER INFORMATION: An exemplary protein sequence of 6H-tagged
      resilin (exon 1) fused to a cellulose-binding domain (CBD)

<400> SEQUENCE: 13

```
Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
                85                  90                  95
```

```
Tyr Gly Ala Pro Gly Gly Gly Asn Gly Asn Gly Gly Arg Pro Ser Ser
            100                 105                 110

Ser Tyr Gly Ala Pro Gly Gly Gly Asn Gly Gly Arg Pro Ser Asp Thr
        115                 120                 125

Tyr Gly Ala Pro Gly Gly Gly Asn Gly Gly Arg Pro Ser Asp Thr Tyr
    130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Gly Arg
        165                 170                 175

Ser Ser Ser Ser Tyr Gly Ala Pro Gly Gly Gly Asn Gly Gly Arg Pro
        180                 185                 190

Ser Asp Thr Tyr Gly Ala Pro Gly Gly Gly Asn Gly Gly Arg Pro Ser
        195                 200                 205

Asp Thr Tyr Gly Ala Pro Gly Gly Gly Asn Asn Gly Gly Arg Pro Ser
        210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
        275                 280                 285

Ser Asp Ser Tyr Gly Ala Pro Gly Ser Gly Asn Gly Asn Gly Gly Arg
        290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Gly Ile
            340                 345                 350

Pro Asp Pro Gly Met Ala Ala Thr Ser Ser Met Ser Val Glu Phe Tyr
        355                 360                 365

Asn Ser Asn Lys Ser Ala Gln Thr Asn Ser Ile Thr Pro Ile Ile Lys
        370                 375                 380

Ile Thr Asn Thr Ser Asp Ser Asp Leu Asn Leu Asn Asp Val Lys Val
385                 390                 395                 400

Arg Tyr Tyr Tyr Thr Ser Asp Gly Thr Gln Gly Gln Thr Phe Trp Cys
                405                 410                 415

Asp His Ala Gly Ala Leu Leu Gly Asn Ser Tyr Val Asp Asn Thr Ser
            420                 425                 430

Lys Val Thr Ala Asn Phe Val Lys Glu Thr Ala Ser Pro Thr Ser Thr
        435                 440                 445

Tyr Asp Thr Tyr Val Glu Phe Gly Phe Ala Ser Gly Arg Ala Thr Leu
        450                 455                 460

Lys Lys Gly Gln Phe Ile Thr Ile Gln Gly Arg Ile Thr Lys Ser Asp
465                 470                 475                 480

Trp Ser Asn Tyr Thr Gln Thr Asn Asp Tyr Ser Phe Asp Ala Ser Ser
            485                 490                 495

Ser Thr Pro Val Val Asn Pro Lys Val Thr Gly Tyr Ile Gly Gly Ala
            500                 505                 510
```

Lys Val Leu Gly Thr Ala Pro
        515

<210> SEQ ID NO 14
<211> LENGTH: 1620
<212> TYPE: DNA
<213> ORGANISM: Artificial sequence
<220> FEATURE:
<223> OTHER INFORMATION: An exemplary DNA sequence of 6H-tagged resilin
      (exon 1) fused to a cellulose-binding domain (CBD)

<400> SEQUENCE: 14

| | | | | | |
|---|---|---|---|---|---|
| catatgtcgt | actaccatca | ccatcaccat | cacgattacg | atatcccaac | gaccgaaaac | 60 |
| ctgtattttc | agggcgccat | ggcagcgaca | tcatcaatgt | cagttgaatt | ttacaactct | 120 |
| aacaaagcag | cacaaacaaa | ctcaattaca | ccaataatca | aaattactaa | cacagctgac | 180 |
| agtgatttaa | atttaaatga | cgtaaaagtt | agatattatt | acacaagtga | tggtacacaa | 240 |
| ggacaaactt | tctggggtga | tcatgctggt | gcattattag | aaatagcta | tgttgataac | 300 |
| actggcaaag | tgacagcaaa | cttcgttaaa | gaaacagcaa | gcccaacatc | aacctatgat | 360 |
| acatatgttg | aatttggatt | tgcaagcgga | gcagctactc | ttaaaaaagg | acaatttata | 420 |
| actattcaag | aagaataac | aaaatcagac | tggtcaaact | acgctcagac | aaatgactat | 480 |
| tcatttgatg | caagtagttc | aacaccagtt | gtaaatccaa | aagttacagg | atatataggt | 540 |
| ggagctaaag | tacttggtac | agcaccaggt | ccagatgtac | catcttcaat | aattaatcct | 600 |
| acttctgcaa | catttgatcc | ggagccacca | gttaactcgt | atctacctcc | gtccgatagc | 660 |
| tatgagcac | cgggtcagag | tggtcccggc | ggcaggccgt | cggattccta | tggagctcct | 720 |
| ggtggtggaa | acggtggacg | gccctcagac | agctatggcg | ctccaggcca | gggtcaagga | 780 |
| cagggacaag | gacaaggtgg | atatgcaggc | aagccctcag | ataccctatgg | agctcctggt | 840 |
| ggtggaaatg | gcaacggagg | tcgtccatcg | agcagctatg | gcgctcctgg | cggtggaaac | 900 |
| ggtggtcgtc | cttcggatac | ctacggtgct | cctggtggcg | gaaatggtgg | acgcccatcg | 960 |
| gacacttatg | gtgctcctgg | tggtggtgga | aatggcaacg | gcggacgacc | ttcaagcagc | 1020 |
| tatggagctc | ctggtcaagg | acaaggcaac | ggaaatggcg | gtcgctcatc | gagcagctat | 1080 |
| ggtgctcctg | gcggtggaaa | cggcggtcgt | ccttcggata | cctacggtgc | tcccggtggt | 1140 |
| ggaaacggtg | gtcgtccttc | ggatacttac | ggcgctcctg | gtggcggcaa | taatggcggt | 1200 |
| cgtccctcaa | gcagctacgg | cgctcctggt | ggtggaaacg | gtggtcgtcc | atctgacacc | 1260 |
| tatggcgctc | ctggtggcgg | taacggaaac | ggcagcggtg | gtcgtccttc | aagcagctat | 1320 |
| ggagctcctg | gtcagggcca | aggtggattt | ggtggtcgtc | catcggactc | ctatggtgct | 1380 |
| cctggtcaga | accaaaaacc | atcagattca | tatggcgccc | ctggtagcgg | caatggcaac | 1440 |
| ggcggacgtc | cttcgagcag | ctatggagct | ccaggctcag | gacctggtgg | ccgaccctcc | 1500 |
| gactcctacg | accccagc | ttctggatcg | ggagcaggtg | gcgctggagg | cagtggaccc | 1560 |
| ggcggcgctg | actacgataa | cgatgagtaa | ggatccgagc | tccgtcgaca | agcttgcggc | 1620 |

<210> SEQ ID NO 15
<211> LENGTH: 528
<212> TYPE: PRT
<213> ORGANISM: Artificial sequence
<220> FEATURE:
<223> OTHER INFORMATION: An exemplary protein sequence of 6H-tagged
      resilin (exon 1) fused to a cellulose-binding domain (CBD)

<400> SEQUENCE: 15

```
Met Ser Tyr Tyr His His His His His His Asp Tyr Asp Ile Pro Thr
1               5                   10                  15

Thr Glu Asn Leu Tyr Phe Gln Gly Ala Met Ala Ala Thr Ser Ser Met
            20                  25                  30

Ser Val Glu Phe Tyr Asn Ser Asn Lys Ala Ala Gln Thr Asn Ser Ile
        35                  40                  45

Thr Pro Ile Ile Lys Ile Thr Asn Thr Ala Asp Ser Asp Leu Asn Leu
    50                  55                  60

Asn Asp Val Lys Val Arg Tyr Tyr Tyr Thr Ser Asp Gly Thr Gln Gly
65                  70                  75                  80

Gln Thr Phe Trp Gly Asp His Ala Gly Ala Leu Leu Gly Asn Ser Tyr
                85                  90                  95

Val Asp Asn Thr Gly Lys Val Thr Ala Asn Phe Val Lys Glu Thr Ala
            100                 105                 110

Ser Pro Thr Ser Thr Tyr Asp Thr Tyr Val Glu Phe Gly Phe Ala Ser
        115                 120                 125

Gly Ala Ala Thr Leu Lys Lys Gly Gln Phe Ile Thr Ile Gln Gly Arg
    130                 135                 140

Ile Thr Lys Ser Asp Trp Ser Asn Tyr Ala Gln Thr Asn Asp Tyr Ser
145                 150                 155                 160

Phe Asp Ala Ser Ser Thr Pro Val Val Asn Pro Lys Val Thr Gly Tyr
                165                 170                 175

Tyr Ile Gly Gly Ala Lys Val Leu Gly Thr Ala Pro Gly Pro Asp Val
            180                 185                 190

Pro Ser Ser Ile Ile Asn Pro Thr Ser Ala Thr Phe Asp Pro Glu Pro
    195                 200                 205

Pro Val Asn Ser Tyr Leu Pro Pro Ser Asp Ser Tyr Gly Ala Pro Gly
210                 215                 220

Gln Ser Gly Pro Gly Gly Arg Pro Ser Asp Ser Tyr Gly Ala Pro Gly
225                 230                 235                 240

Gly Gly Asn Gly Gly Arg Pro Ser Asp Ser Tyr Gly Ala Pro Gly Gln
                245                 250                 255

Gly Gln Gly Gln Gly Gln Gly Gln Gly Gly Tyr Ala Gly Lys Pro Ser
            260                 265                 270

Asp Thr Tyr Gly Ala Pro Gly Gly Gly Asn Gly Asn Gly Gly Arg Pro
    275                 280                 285

Ser Ser Ser Tyr Gly Ala Pro Gly Gly Gly Asn Gly Gly Arg Pro Ser
290                 295                 300

Asp Thr Tyr Gly Ala Pro Gly Gly Gly Asn Gly Gly Arg Pro Ser Asp
305                 310                 315                 320

Thr Tyr Gly Ala Pro Gly Gly Gly Asn Gly Asn Gly Gly Arg Pro
                325                 330                 335

Ser Ser Ser Tyr Gly Ala Pro Gly Gln Gly Gln Gly Asn Gly Asn Gly
            340                 345                 350

Gly Arg Ser Ser Ser Tyr Gly Ala Pro Gly Gly Gly Asn Gly Gly
    355                 360                 365

Arg Pro Ser Asp Thr Tyr Gly Ala Pro Gly Gly Gly Asn Gly Gly Arg
370                 375                 380

Pro Ser Asp Thr Tyr Gly Ala Pro Gly Gly Asn Asn Gly Gly Arg
385                 390                 395                 400

Pro Ser Ser Ser Tyr Gly Ala Pro Gly Gly Asn Gly Gly Arg Pro
                405                 410                 415

Ser Asp Thr Tyr Gly Ala Pro Gly Gly Gly Asn Gly Asn Gly Ser Gly
```

```
                420                 425                 430

Gly Arg Pro Ser Ser Tyr Gly Ala Pro Gly Gln Gly Gln Gly Gly
            435                 440                 445

Phe Gly Gly Arg Pro Ser Asp Ser Tyr Gly Ala Pro Gly Gln Asn Gln
        450                 455                 460

Lys Pro Ser Asp Ser Tyr Gly Ala Pro Gly Ser Gly Asn Gly Asn Gly
465                 470                 475                 480

Gly Arg Pro Ser Ser Tyr Gly Ala Pro Gly Ser Gly Pro Gly Gly
            485                 490                 495

Arg Pro Ser Asp Ser Tyr Gly Pro Ala Ser Gly Ser Gly Ala Gly
        500                 505                 510

Gly Ala Gly Gly Ser Gly Pro Gly Gly Ala Asp Tyr Asp Asn Asp Glu
        515                 520                 525

<210> SEQ ID NO 16
<211> LENGTH: 324
<212> TYPE: PRT
<213> ORGANISM: Artificial sequence
<220> FEATURE:
<223> OTHER INFORMATION: Resilin exon 1

<400> SEQUENCE: 16

Gly Pro Glu Pro Pro Val Asn Ser Tyr Leu Pro Pro Ser Asp Ser Tyr
1               5                   10                  15

Gly Ala Pro Gly Gln Ser Gly Pro Gly Arg Pro Ser Asp Ser Tyr
            20                  25                  30

Gly Ala Pro Gly Gly Asn Gly Gly Arg Pro Ser Asp Ser Tyr Gly
        35                  40                  45

Ala Pro Gly Gln Gly Gln Gly Gln Gly Gln Gly Gly Tyr Ala
    50                  55                  60

Gly Lys Pro Ser Asp Thr Tyr Gly Ala Pro Gly Gly Asn Gly Asn
65                  70                  75                  80

Gly Gly Arg Pro Ser Ser Tyr Gly Ala Pro Gly Gly Asn Gly
            85                  90                  95

Gly Arg Pro Ser Asp Thr Tyr Gly Ala Pro Gly Gly Asn Gly Gly
        100                 105                 110

Arg Pro Ser Asp Thr Tyr Gly Ala Pro Gly Gly Gly Asn Gly Asn
        115                 120                 125

Gly Gly Arg Pro Ser Ser Tyr Gly Ala Pro Gly Gln Gly Gln Gly
        130                 135                 140

Asn Gly Asn Gly Gly Arg Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
        165                 170                 175

Asn Gly Gly Arg Pro Ser Asp Thr Tyr Gly Ala Pro Gly Gly Asn
            180                 185                 190

Asn Gly Gly Arg Pro Ser Ser Tyr Gly Ala Pro Gly Gly Gly Asn
        195                 200                 205

Gly Gly Arg Pro Ser Asp Thr Tyr Gly Ala Pro Gly Gly Gly Asn Gly
        210                 215                 220

Asn Gly Ser Gly Gly Arg Pro Ser Ser Tyr Gly Ala Pro Gly Gln
225                 230                 235                 240

Gly Gln Gly Gly Phe Gly Gly Arg Pro Ser Asp Ser Tyr Gly Ala Pro
            245                 250                 255

Gly Gln Asn Gln Lys Pro Ser Asp Ser Tyr Gly Ala Pro Gly Ser Gly
```

```
                    260                 265                 270

Asn Gly Asn Gly Gly Arg Pro Ser Ser Tyr Gly Ala Pro Gly Ser
                275                 280                 285

Gly Pro Gly Gly Arg Pro Ser Asp Ser Tyr Gly Pro Pro Ala Ser Gly
                290                 295                 300

Ser Gly Ala Gly Gly Ala Gly Ser Gly Pro Gly Ala Asp Tyr
305                 310                 315                 320

Asp Asn Asp Glu

<210> SEQ ID NO 17
<211> LENGTH: 180
<212> TYPE: PRT
<213> ORGANISM: Artificial sequence
<220> FEATURE:
<223> OTHER INFORMATION: Cellulose binding domain protein sequence

<400> SEQUENCE: 17

Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
                20                  25                  30

Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
        50                  55                  60

Ala Leu Leu Gly Asn Ser Tyr Val Asp Asn Thr Gly Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Ala Gln Thr Asn Asp Tyr Ser Phe Asp Ala Ser Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro Gly Pro Asp Val Pro Ser Ser Ile Ile Asn Pro Thr Ser
                165                 170                 175

Ala Thr Phe Asp
            180

<210> SEQ ID NO 18
<211> LENGTH: 163
<212> TYPE: PRT
<213> ORGANISM: Artificial sequence
<220> FEATURE:
<223> OTHER INFORMATION: Cellulose binding domain protein sequence

<400> SEQUENCE: 18

Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
                20                  25                  30

Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
```

```
                    50                  55                  60
Ala Leu Leu Gly Asn Ser Tyr Val Asp Asn Thr Gly Lys Val Thr Ala
 65                  70                  75                  80

Asn Phe Val Lys Glu Thr Ala Ser Pro Thr Ser Thr Tyr Asp Thr Tyr
                 85                  90                  95

Val Glu Phe Gly Phe Ala Ser Gly Ala Ala Thr Leu Lys Lys Gly Gln
                100                 105                 110

Phe Ile Thr Ile Gln Gly Arg Ile Thr Lys Ser Asp Trp Ser Asn Tyr
                115                 120                 125

Ala Gln Thr Asn Asp Tyr Ser Phe Asp Ala Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro

<210> SEQ ID NO 19
<211> LENGTH: 605
<212> TYPE: PRT
<213> ORGANISM: Drosophila melanogaster

<400> SEQUENCE: 19

Met Val Arg Pro Glu Pro Pro Val Asn Ser Tyr Leu Pro Pro Ser Asp
  1               5                  10                  15

Ser Tyr Gly Ala Pro Gly Gln Ser Gly Pro Gly Gly Arg Pro Ser Asp
                 20                  25                  30

Ser Tyr Gly Ala Pro Gly Gly Asn Gly Gly Arg Pro Ser Asp Ser
             35                  40                  45

Tyr Gly Ala Pro Gly Gln Gly Gln Gly Gln Gly Gln Gly Gln Gly Gly
 50                  55                  60

Tyr Ala Gly Lys Pro Ser Asp Thr Tyr Gly Ala Pro Gly Gly Gly Asn
 65                  70                  75                  80

Gly Asn Gly Gly Arg Pro Ser Ser Ser Tyr Gly Ala Pro Gly Gly Gly
                 85                  90                  95

Asn Gly Gly Arg Pro Ser Asp Thr Tyr Gly Ala Pro Gly Gly Gly Asn
                100                 105                 110

Gly Gly Arg Pro Ser Asp Thr Tyr Gly Ala Pro Gly Gly Gly Gly Asn
            115                 120                 125

Gly Asn Gly Gly Arg Pro Ser Ser Ser Tyr Gly Ala Pro Gly Gln Gly
            130                 135                 140

Gln Gly Asn Gly Asn Gly Gly Arg Ser Ser Ser Tyr Gly Ala Pro
145                 150                 155                 160

Gly Gly Gly Asn Gly Gly Arg Pro Ser Asp Thr Tyr Gly Ala Pro Gly
                165                 170                 175

Gly Gly Asn Gly Gly Arg Pro Ser Asp Thr Tyr Gly Ala Pro Gly Gly
            180                 185                 190

Gly Asn Asn Gly Gly Arg Pro Ser Ser Ser Tyr Gly Ala Pro Gly Gly
            195                 200                 205

Gly Asn Gly Gly Arg Pro Ser Asp Thr Tyr Gly Ala Pro Gly Gly Gly
            210                 215                 220

Asn Gly Asn Gly Ser Gly Gly Arg Pro Ser Ser Ser Tyr Gly Ala Pro
225                 230                 235                 240

Gly Gln Gly Gln Gly Gly Phe Gly Gly Arg Pro Ser Asp Ser Tyr Gly
                245                 250                 255

Ala Pro Gly Gln Asn Gln Lys Pro Ser Asp Ser Tyr Gly Ala Pro Gly
```

```
                    260                 265                 270
Ser Gly Asn Gly Asn Gly Gly Arg Pro Ser Ser Ser Tyr Gly Ala Pro
            275                 280                 285
Gly Ser Gly Pro Gly Gly Arg Pro Ser Asp Ser Tyr Gly Pro Pro Ala
            290                 295                 300
Ser Gly Ser Gly Ala Gly Gly Ala Gly Gly Ser Gly Pro Gly Gly Ala
305                 310                 315                 320
Asp Tyr Asp Asn Asp Glu Pro Ala Lys Tyr Glu Phe Asn Tyr Gln Val
            325                 330                 335
Glu Asp Ala Pro Ser Gly Leu Ser Phe Gly His Ser Glu Met Arg Asp
            340                 345                 350
Gly Asp Phe Thr Thr Gly Gln Tyr Asn Val Leu Leu Pro Asp Gly Arg
            355                 360                 365
Lys Gln Ile Val Glu Tyr Glu Ala Asp Gln Gln Gly Tyr Arg Pro Gln
            370                 375                 380
Ile Arg Tyr Glu Gly Asp Ala Asn Asp Gly Ser Gly Pro Ser Gly Pro
385                 390                 395                 400
Gly Gly Pro Gly Gly Gln Asn Leu Gly Ala Asp Gly Tyr Ser Ser Gly
            405                 410                 415
Arg Pro Gly Asn Gly Asn Gly Asn Gly Asn Gly Gly Tyr Ser Gly Gly
            420                 425                 430
Arg Pro Gly Gly Gln Asp Leu Gly Pro Ser Gly Tyr Ser Gly Gly Arg
            435                 440                 445
Pro Gly Gly Gln Asp Leu Gly Ala Gly Gly Tyr Ser Asn Gly Lys Pro
            450                 455                 460
Gly Gly Gln Asp Leu Gly Pro Gly Gly Tyr Ser Gly Gly Arg Pro Gly
465                 470                 475                 480
Gly Gln Asp Leu Gly Arg Asp Gly Tyr Ser Gly Gly Arg Pro Gly Gly
            485                 490                 495
Gln Asp Leu Gly Ala Ser Gly Tyr Ser Asn Gly Arg Pro Gly Gly Asn
            500                 505                 510
Gly Asn Gly Gly Ser Asp Gly Gly Arg Val Ile Ile Gly Gly Arg Val
            515                 520                 525
Ile Gly Gly Gln Asp Gly Gly Asp Gln Gly Tyr Ser Gly Gly Arg Pro
            530                 535                 540
Gly Gly Gln Asp Leu Gly Arg Asp Gly Tyr Ser Ser Gly Arg Pro Gly
545                 550                 555                 560
Gly Arg Pro Gly Gly Asn Gly Gln Asp Ser Gln Asp Gly Gln Gly Tyr
            565                 570                 575
Ser Ser Gly Arg Pro Gly Gln Gly Gly Arg Asn Gly Phe Gly Pro Gly
            580                 585                 590
Gly Gln Asn Gly Asp Asn Asp Gly Ser Gly Tyr Arg Tyr
            595                 600                 605
```

UNITED STATES PATENT AND TRADEMARK OFFICE
CERTIFICATE OF CORRECTION

PATENT NO. : 10,799,616 B2  
APPLICATION NO. : 15/034646  
DATED : October 13, 2020  
INVENTOR(S) : Oded Shoseyov et al.

Page 1 of 1

It is certified that error appears in the above-identified patent and that said Letters Patent is hereby corrected as shown below:

In the Claims

In Claim 1, Column 69 at Line 62, after "via at least one" the following should be added --amide bond--.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*